United States Patent
Buschmann

(10) Patent No.: US 10,611,656 B2
(45) Date of Patent: *Apr. 7, 2020

(54) METHODS OF MICROBIAL CONTROL

(71) Applicant: Clean Chemistry, Inc., Boulder, CO (US)

(72) Inventor: Wayne E. Buschmann, Boulder, CO (US)

(73) Assignee: Clean Chemistry, Inc., Boulder, CO (US)

( * ) Notice: Subject to any disclaimer, the term of this patent is extended or adjusted under 35 U.S.C. 154(b) by 348 days.

This patent is subject to a terminal disclaimer.

(21) Appl. No.: 15/371,567

(22) Filed: Dec. 7, 2016

(65) Prior Publication Data

US 2017/0158537 A1 Jun. 8, 2017

Related U.S. Application Data

(60) Provisional application No. 62/263,900, filed on Dec. 7, 2015.

(51) Int. Cl.
*C02F 1/00* (2006.01)
*C02F 1/02* (2006.01)
(Continued)

(52) U.S. Cl.
CPC .......... *C02F 9/00* (2013.01); *C02F 1/722* (2013.01); *C12P 3/00* (2013.01); *D21C 9/166* (2013.01);
(Continued)

(58) Field of Classification Search
CPC .... C02F 1/008; C02F 1/02; C02F 1/50; C02F 1/722; C02F 1/76; C02F 1/766;
(Continued)

(56) References Cited

U.S. PATENT DOCUMENTS

| 3,719,552 A | 3/1973 | Farley |
| 3,925,234 A | 12/1975 | Hachmann et al. |

(Continued)

FOREIGN PATENT DOCUMENTS

| CN | 1142555 | 2/1997 |
| CN | 102007230 | 4/2011 |

(Continued)

OTHER PUBLICATIONS

Suihko et al.; "A study of the microflora of some recycled fibre pulps, boards and kitchen rolls;" Journal of Applied Microbiology; 1997; 83; pp. 199-207.

(Continued)

*Primary Examiner* — Lucas A Stelling
(74) *Attorney, Agent, or Firm* — Snell & Wilmer L.L.P.

(57) ABSTRACT

In some embodiments, a method may include reducing the microbial load in contaminated water of water recycle loops. These water recycling loops may include pulp and paper mills, cooling towers and water loops, evaporation ponds, feedstock processing systems and/or non-potable water systems. The methods may include providing a peracetate oxidant solution. The peracetate solution may include peracetate anions and a peracid. In some embodiments, the peracetate solution may include a pH from about pH 10 to about pH 12. In some embodiments, the peracetate solution has a molar ratio of peracetate anions to peracid ranging from about 60:1 to about 6000:1. In some embodiments, the peracetate solution has a molar ratio of peracetate to hydrogen peroxide of greater than about 16:1. The peracetate solution may provide bleaching, sanitizing and/or disinfection of contaminated water and surfaces. The peracetate oxidant solution may provide enhanced separation of microbes from contaminated water.

13 Claims, 4 Drawing Sheets

(51) Int. Cl.
*C02F 1/50* (2006.01)
*C02F 1/72* (2006.01)
*C02F 1/76* (2006.01)
*C12P 3/00* (2006.01)
*D21C 9/16* (2006.01)
*C02F 9/00* (2006.01)
*C02F 103/28* (2006.01)
*C02F 103/32* (2006.01)
*C02F 103/00* (2006.01)
*C02F 103/02* (2006.01)

(52) U.S. Cl.
CPC .............. *C02F 1/008* (2013.01); *C02F 1/02* (2013.01); *C02F 1/50* (2013.01); *C02F 1/76* (2013.01); *C02F 1/766* (2013.01); *C02F 2103/007* (2013.01); *C02F 2103/023* (2013.01); *C02F 2103/28* (2013.01); *C02F 2103/32* (2013.01); *C02F 2209/04* (2013.01); *C02F 2209/36* (2013.01); *C02F 2303/02* (2013.01); *C02F 2303/04* (2013.01); *C02F 2303/08* (2013.01); *C02F 2303/20* (2013.01)

(58) Field of Classification Search
CPC ................ C02F 9/00; C02F 2103/007; C02F 2103/023; C02F 2103/28; C02F 2103/32; C02F 2209/04; C02F 2209/36; C02F 2303/02; C02F 2303/04; C02F 2303/08; C02F 2303/20; C12P 3/00; D21C 9/166
See application file for complete search history.

(56) References Cited

U.S. PATENT DOCUMENTS

| | | |
|---|---|---|
| 4,055,505 A | 10/1977 | Gray |
| 4,076,621 A | 2/1978 | Hardison |
| 4,348,256 A | 9/1982 | Bergstrom, Jr. et al. |
| 4,393,037 A | 7/1983 | Delaney et al. |
| 4,576,609 A | 3/1986 | Hageman |
| 4,673,473 A | 6/1987 | Ang et al. |
| 4,722,773 A | 2/1988 | Plowman et al. |
| 4,952,276 A | 8/1990 | Gidlund |
| 4,966,706 A | 10/1990 | Gregor |
| 5,053,142 A | 10/1991 | Sorensen et al. |
| 5,246,543 A | 9/1993 | Meier et al. |
| 5,387,317 A | 2/1995 | Parthasarathy et al. |
| 5,424,032 A | 6/1995 | Christensen et al. |
| 5,431,781 A | 7/1995 | Walsh |
| 5,472,619 A | 12/1995 | Holzhauer et al. |
| 5,494,588 A | 2/1996 | LaZonby |
| 5,565,073 A | 10/1996 | Fraser et al. |
| 5,683,724 A | 11/1997 | Hei et al. |
| 5,770,035 A | 6/1998 | Faita |
| 5,785,812 A | 7/1998 | Linsten et al. |
| 5,817,240 A | 10/1998 | Miller et al. |
| 6,007,678 A | 12/1999 | Linsten et al. |
| 6,015,536 A | 1/2000 | Lokkesmoe et al. |
| 6,126,782 A | 10/2000 | Liden et al. |
| 6,183,623 B1 | 2/2001 | Cisar et al. |
| 6,258,207 B1 | 7/2001 | Pan |
| 6,387,238 B1 | 5/2002 | Merk et al. |
| 6,569,286 B1 | 5/2003 | Withenshaw et al. |
| 6,712,949 B2 | 3/2004 | Gopal |
| 8,318,972 B2 | 11/2012 | Buschmann et al. |
| 9,517,955 B2 | 12/2016 | Buschmann |
| 9,517,956 B2 | 12/2016 | Buschmann |
| 9,551,076 B2 | 1/2017 | Buschmann |
| 10,259,729 B2 | 4/2019 | Buschmann |
| 2001/0050234 A1 | 12/2001 | Shiepe |
| 2002/0153262 A1 | 10/2002 | Uno et al. |
| 2003/0019757 A1 | 1/2003 | Vetrovec |
| 2003/0019758 A1 | 1/2003 | Gopal |
| 2003/0024054 A1 | 2/2003 | Burns |
| 2004/0112555 A1 | 6/2004 | Tolan et al. |
| 2004/0134857 A1 | 7/2004 | Huling et al. |
| 2004/0200588 A1 | 10/2004 | Walker |
| 2005/0183949 A1 | 8/2005 | Daly |
| 2006/0207734 A1 | 9/2006 | Day |
| 2007/0074975 A1* | 4/2007 | Buschmann .......... C02F 1/4672 205/466 |
| 2007/0212594 A1 | 9/2007 | Takasu et al. |
| 2007/0243449 A1 | 10/2007 | Sotomura et al. |
| 2009/0012346 A1 | 1/2009 | Al Nashef et al. |
| 2009/0090478 A1 | 4/2009 | Hollomon et al. |
| 2009/0152123 A1 | 6/2009 | Butler et al. |
| 2009/0285738 A1 | 11/2009 | Winter et al. |
| 2009/0314652 A1 | 12/2009 | Buschmann et al. |
| 2010/0078331 A1 | 4/2010 | Scherson et al. |
| 2010/0160449 A1 | 6/2010 | Rovison, Jr. et al. |
| 2010/0176066 A1 | 7/2010 | Budde et al. |
| 2010/0179368 A1 | 7/2010 | Conrad |
| 2011/0017066 A1 | 1/2011 | Takeuchi et al. |
| 2011/0024361 A1 | 2/2011 | Schwartzel et al. |
| 2011/0123642 A1 | 5/2011 | Wilmotte |
| 2011/0232853 A1 | 9/2011 | Yin |
| 2012/0067532 A1 | 3/2012 | Lee |
| 2012/0091069 A1 | 4/2012 | Fischmann |
| 2012/0108878 A1 | 5/2012 | Conrad |
| 2012/0145643 A1 | 6/2012 | Pandya |
| 2012/0240647 A1 | 9/2012 | Montemurro |
| 2012/0267315 A1 | 10/2012 | Soane et al. |
| 2012/0322873 A1 | 12/2012 | Atkins et al. |
| 2013/0064484 A1 | 3/2013 | LeBlanc et al. |
| 2013/0259743 A1 | 10/2013 | Keasler et al. |
| 2013/0264293 A1 | 10/2013 | Keasler et al. |
| 2014/0069821 A1 | 3/2014 | Marcin et al. |
| 2014/0072653 A1 | 3/2014 | Buschmann |
| 2014/0131217 A1 | 5/2014 | Buschmann |
| 2014/0131259 A1 | 5/2014 | Goldblatt |
| 2014/0197102 A1* | 7/2014 | Van Der Wal ........ C02F 1/4691 210/638 |
| 2014/0205777 A1 | 7/2014 | Hawkins et al. |
| 2014/0238626 A1 | 8/2014 | Tsuji et al. |
| 2014/0374104 A1 | 12/2014 | Seth |
| 2016/0068417 A1 | 3/2016 | Buschmann |
| 2016/0297697 A1 | 10/2016 | Buschmann |
| 2016/0318778 A1 | 11/2016 | Buschmann |
| 2017/0051417 A1 | 2/2017 | Buschmann |
| 2017/0107128 A1 | 4/2017 | Buschmann |
| 2017/0114468 A1 | 4/2017 | Buschmann |
| 2017/0158537 A1 | 6/2017 | Buschmann |
| 2017/0159237 A1 | 6/2017 | Buschmann |
| 2018/0023250 A1 | 1/2018 | Buschmann |

FOREIGN PATENT DOCUMENTS

| | | |
|---|---|---|
| EP | 0480469 A3 | 4/1992 |
| WO | 9739179 A1 | 10/1997 |
| WO | 1999032710 | 7/1999 |
| WO | 2000069778 | 11/2000 |
| WO | 2008056025 A2 | 5/2008 |
| WO | 2010059459 | 5/2010 |
| WO | 2012166997 | 12/2012 |
| WO | 2013060700 A1 | 5/2013 |
| WO | 2013064484 | 5/2013 |
| WO | 9402423 A1 | 2/2014 |
| WO | 2014039929 | 3/2014 |
| WO | 2014100828 | 6/2014 |
| WO | 2016037149 | 3/2016 |
| WO | 2016154531 | 9/2016 |
| WO | 2017100284 | 6/2017 |
| WO | 2017100299 | 6/2017 |

OTHER PUBLICATIONS

Pedros et al.; "Chlorophyll fluorescence emission spectrum inside a leaf"; The Royal Society of Chemistry and Owner Societies; 2008; No. 7; pp. 498-502.

Coyle et al.; "Peracetic Acid as an Alternative Disinfection Technology for Wet Weather Flows"; Water Environment Research; Aug. 2014; pp. 687-697.

(56) References Cited

OTHER PUBLICATIONS

Smook; Chapter 14: Secondary Fiber; Handbook for Pulp & Papers Technologists; Angus Wilde Publications; 2001; pp. 209-219.
U.S. Appl. No. 15/334,012 entitled "Electrochemical Reactor and Process".
U.S. Appl. No. 15/344,080 entitled "System and Method for Generation of Point of Use Reactive Oxygen Species".
U.S. Appl. No. 15/308,966 entitled "System and Method for Generation of Reactive Oxygen Species and Applications Thereof".
U.S. Appl. No. 14/846,123 entitled "Systems and Method of Water Treatement Utilizing Reactive Oxygen Species and Applications Thereof".
U.S. Appl. No. 15/081,411 entitled "Systems and Method of Reducing a Bacteria Population in High Hydrogen Sulfide Water".
U.S. Appl. No. 15/371,872 entitled "Methods of Pulp Fiber Treatment".
U.S. Appl. No. 15/601,350 entitled "Methods of Pulp Fiber Treatment".
U.S. Appl. No. 15/658,709 entitled "Methods of Optical Brightening Agent Removal".
CC15—Suslow, T. "Oxidation-Reduction Potential (ORP) for Water Disinfection Monitoring, Control, and Documentation" Univ. California Publication 8149 http://anrcatalog.ucdavis.edu, Copyright 2004.
Co-Pending U.S. Appl. No. 15/601,350 entitled, "Methods of Pulp Fiber Treatment" to Buschmann filed May 22, 2017.
Co-Pending U.S. Appl. No. 15/658,709 entitled, "Methods of Optical Brigthening Agent Removal" to Buschmann filed Jul. 25, 2017.
CC16—L.D. Shackford, "A Comparison of Pulping and Bleaching of Kraft Softwood and Eucalyptus Pulps;" 36th International Pulp and Paper Congress and Exhibition; Oct. 13-16, 2003, Sao Paulo, Brazil.
Notice of Allowance for U.S. Appl. No. 14/122,185 dated Oct. 13, 2016.
Notice of Allowance for U.S. Appl. No. 14/020,828 dated Aug. 11, 2016.
CC06—International Preliminary Report on Patentability for PCT/US2013/058650 dated Jan. 29, 2014.
CC07—Australian Examination Report No. 1 for 2013312249 dated Mar. 17, 2017.
CC08—Second Office Action for Chinese Application No. 2013800580496 dated Sep. 18, 2016.
CC09—Extended European Search Report for European Application No. EP 13 83 4576 dated Oct. 4, 2016.
Notice of Allowance for U.S. Appl. No. 15/206,901 dated Aug. 17, 2016.
Restriction for U.S. Appl. No. 14/846,123 dated Sep. 7, 2017.
CC10—International Preliminary Report on Patentability for PCT/US2015/048722 dated Feb. 8, 2016.
CC11—International Preliminary Report on Patentability for PCT/US2016/024207 dated Sep. 26, 2017.
CC12—International Search Report for PCT/US2016/065326 dated Feb. 24, 2017.
Non-Final Office Action for U.S. Appl. No. 15/371,872 dated Oct. 12, 2017.
CC13—International Search Report for PCT/US2016/065345 dated Feb. 17, 2017.
CC14—International Search Report for PCT/US2017/033824 dated Aug. 29, 2017.
CC01—International Search Report for PCT/US2012/040325 dated Feb. 1, 2013.
Non-Final Office Action for U.S. Appl. No. 14/122,185 dated Oct. 28, 2015.
Final Office Action for U.S. Appl. No. 14/122,185 dated Jul. 28, 2016.
Non-Final Office Action for U.S. Appl. No. 14/020,828 dated Jan. 20, 2016.
Notice of Allowance for U.S. Appl. No. 14/020,828 dated Mar. 30, 2016.
CC02—International Search Report for PCT/US2013/058650 dated Jan. 29, 2014.
CC03—First Office Action for Chinese Application No. 2013800580496 dated Feb. 4, 2016.
CC05—Supplementary Partial European Search Report for European Application No. EP 13 83 4576 dated May 10, 2016.
CC04—International Search Report for PCT/US2015/048722 dated Feb. 8, 2016.
Verween et al.; "Comparative toxicity of chlorine and peracetic acid in the biofouling control of Mytilopsis leucophaeata and Dreissena polymorpha embryos"; International Biodeterioration & Biodegradation; Jun. 1, 2009; vol. 63, No. 4; pp. 523-528.
Gullichsen et al., eds.; Chemical Pulping; Papermaking Science and Technology; Book 6A; 1999; Fapet Oy; pp. A40-A41 and A616-A665.
Hill et al.; "Part 1: Peracetic Acid—An effective alternative for Chlorine compound Free Delignification of Kraft Pulp"; 1992; Pulping Conference; pp. 1219-1230.

* cited by examiner

METHODS OF MICROBIAL CONTROL

PRIORITY CLAIM

This application claims priority to U.S. Provisional Patent Application No. 62/263,900 entitled "METHODS OF MICROBIAL CONTROL" filed on Dec. 7, 2015, all of which is incorporated by reference herein.

BACKGROUND OF THE INVENTION

1. Field of the Invention

The present disclosure generally relates to microbial control using peracetate oxidant solutions. The disclosure more particularly relates to a method of reducing microbial load, disinfecting, and sanitizing contaminated water involving the use of peracetate oxidant solutions.

2. Description of the Relevant Art

Microbial control in water is imperative to a wide variety of processing and manufacturing systems. These systems can include water recycling loops, pulp and paper mills, cooling towers and water loops, feedstock processing systems, evaporation ponds and non-potable water systems. Treatment of water for microbial control in water recycle loops is critical for maintaining efficient processes, protecting equipment from biofouling and biocorrosion, preventing contamination of products, reducing downtime and protecting the health of people exposed to such processes and products. Furthermore, microbial control in water recycle loops also provides odor control by minimizing fermentation, hydrogen sulfide production and algal decomposition.

Microbial control in pulp and paper mills serves to protect the integrity of pulp slurries, coating ingredients, whitewater loop, process equipment, and paper quality. Controlling sessile bacteria helps to prevent the accumulation of biofilm deposits which cause microbiologically influenced corrosion (i.e., biocorrosion). Slime deposits are often a combination of bacteria and fungi. Importantly, when biofilms and their detritus detach from surfaces in the wet end papermaking process, they can cause holes and other defects in finished paper products. Therefore, preventing biofilm growth helps to avoid such defects.

Microbial control in cooling towers and cooling water loops serves to improve cooling efficiency, minimize microbiologically influenced corrosion, control odors, prevent clogging of pumps and pipes, reduce microbial loading in blowdown, and minimize microbial exposure of surrounding areas from drift.

Microbial control may also occur on surfaces serving to bleach, sanitize and/or disinfect the surfaces of a processing or manufacturing system.

Microbial control targets include aerobic and anaerobic bacteria (slime formers, acid producers, metal depositors, nitrobacteria, sulfate reducers, nitrate reducers), fungi, algae, molds, spores and yeast. Some bacteria are pathogenic, for example, *Legionella pneumophila*, which poses health risks. Some algae, such as cyanobacteria, produce algal toxins that pose potential health hazards.

Compounds used for microbial control need to be effective and efficient at neutral and alkaline pH. They also need to be effective at elevated levels of suspended solids (including silt, pulp, fillers, pigments, suspended metals, oils, polymers) and dissolved solids (including salt, scaling minerals, carbonate, dissolved metals, scale inhibitors and other additives that may be encountered in various processes).

Microbial control is generally achieved using chemical biocides. Oxidizing biocides (e.g., chlorine gas, chlorine bleach, iodine, hypobromous acid, chlorine dioxide, chloramines, bromamines, fluorine, peroxyacetic acid, hydrogen peroxide, ozone) are typically fast acting and relatively short lived compared to non-oxidizing biocides (e.g., glutaraldehyde, dodecylguanidine, bromohydroxyacetophenone, bronopol, hydantoins, isothiazolins), which are slower acting, but leave long lasting active residuals that can persist for several weeks in the environment. Commonly used oxidizing biocides are effective in the treatment of water with relatively low levels of contaminants, however significant issues arise when higher concentrations of organic materials and salinity are present. Microbial resistance to chlorine and bromine-based oxidizing biocides is a growing issue in municipal and industrial water systems.

There are numerous tradeoffs in selecting a biocide for specific applications. Chlorine was first used in municipal water treatment in the U.S. in 1909 as a disinfectant. Since then chlorine and chlorine-based biocides have been the standard for large scale municipal and industrial disinfection. Oxidizing biocides based on free chlorine and bromine in water react readily with organic materials to form halogenated disinfection byproducts, which are persistent in the environment and often exhibiting high toxicity. The antimicrobial activity of aqueous chlorine and bromine decreases rapidly above about pH 7 and pH 8, respectively. Chlorine dioxide is an effective biocide over a wider pH range and has a lower potential to form halogenated disinfection byproducts if generated properly. However, byproducts of chlorine dioxide include chlorite and chlorate, which are regulated in drinking water. Peroxyacetic acid (PAA), which is a stabilized mixture of PAA, hydrogen peroxide, acetic acid and water, is an effective biocide, but not as efficient as chlorine dioxide in that higher doses are necessary to achieve similar performance. PAA performance declines as pH becomes more alkaline and promotes non-beneficial decomposition reactions between PAA, hydrogen peroxide and metal contaminants. Hydrogen peroxide by itself has significantly lower antimicrobial efficacy than PAA and halogen-based biocides while microbes can rapidly develop tolerance to it in water recycle loops. PAA and hydrogen peroxide rapidly degrade in the environment and form significantly fewer disinfection byproducts than halogenated biocides. Oxidizing biocides can also directly oxidize odor-causing materials such as phenols, sulfides and mercaptans.

Corrosivity of oxidizing biocides is another issue, especially when the biocides come in contact with various process materials such as steel, copper and brass alloys. Oxidizing biocides used in processes where elevated temperatures and turbulence are present in the liquid phase should ideally have low vapor pressures to minimize vapor phase corrosion of surrounding equipment and structures. Biocide materials that are gases in their native form are the most volatile and present the greatest corrosion and occupational exposure hazards, including chlorine, chlorine dioxide and ozone.

Control of biocide dosing in a process stream by monitoring the oxidation potential of the treated water is an advantage for real-time process control. The oxidation-reduction potential (ORP) of a solution can be correlated with a level of biocidal control at a given pH and often with the concentration of active biocide present (and corresponding corrosivity). Various forms of chlorine, bromine, chlorine dioxide and sometimes ozone can provide a strong ORP response when used at low concentrations at neutral to moderately alkaline pH. For example, the ORP of chlorine bleach or chlorine dioxide at a 1-2 ppm concentration in relatively clean fresh water at pH 7 can exceed 700 mV vs standard hydrogen electrode (ORP greater than 650 mV typically provides effective bacteria control). In contrast, PAA, hydrogen peroxide and non-oxidizing biocides do not provide a meaningful ORP response above a dissolved oxygen background in fresh water, which is about 420-520 mV at pH 7.

There is a need for highly effective and fast acting oxidizing biocides that are safer to use, have lower environmental impacts and contribute to pollution prevention efforts. Water-based alkyl peroxide salt solutions that efficiently produce reactive oxygen species (ROS) are a class of highly active oxidants that provide multiple biocidal species, have low volatility, degrade to benign residuals, can be produced from stable feedstocks under mild conditions, and reduce or eliminate several harmful disinfection and oxidation byproducts.

It is desirable to find an efficient and cost effective method of microbial control in water of process systems.

SUMMARY

In some embodiments, a method provides for microbial control by reducing the microbial load in contaminated water of water recycle loops. These water recycling loops include pulp and paper mills, cooling towers and water loops, evaporation ponds, feedstock processing systems and non-potable water systems. The methods may include providing a peracetate oxidant solution. The peracetate solution may include peracetate anions and a peracid. In some embodiments, the peracetate solution may include a pH from about pH 10 to about pH 12. In some embodiments, the peracetate solution has a molar ratio of peracetate anions to peracid ranging from about 60:1 to about 6000:1. In some embodiments, the peracetate solution has a molar ratio of peracetate to hydrogen peroxide of greater than about 16:1. The peracetate solution may provide bleaching, sanitizing and/or disinfection of contaminated water and surfaces. The peracetate oxidant solution may provide enhanced separation of microbes from contaminated water. In some embodiments, the peracetate oxidant solution kills the microbial population in the contaminated water. In some embodiments, the microbes are removed from the contaminated water. In some embodiments, the peracetate solution reduces the biofilms and microbial corrosion.

In some embodiments, a method provides for microbial control and reduction of oxidation byproducts in water treatment, cooling water loops, bleaching and paper making using highly active peracetate oxidant solutions.

In some embodiments, the contaminated water comprises impurities, and wherein separating the microbes and water phase comprises separating the microbe and water phase into at least microbes, impurities and water.

In some embodiments, the amount of peracetate oxidant solution used is dependent on the severity of contamination, the degree of microbial control desired and residual oxidant solution necessary for effective microbial control.

In some embodiments, the contaminated water can be sequentially dosed with peracetate oxidant solution until the degree of microbial control desired is reached and the sequential dosing has a synergistic effect on microbial control. The reducing of the microbial load prevents bacteria in the contaminated water from becoming anaerobic and prevents the formation of sulfides, ammonia, volatile organic acids which result in reduced release of volatile materials and odor control.

In some embodiments, a method is provided for the ability to combine the use of peracetate oxidant solution and an alternative oxidant for improved antimicrobial treatment of water. In some embodiments, the alternative oxidant is selected from the group consisting of chlorine, chlorine bleach, bromine, iodine and fluorine.

In some embodiments, a method is provided for reducing the microbial load in contaminated water previously treated with an alternative oxidant by treating with a peracetate oxidant solution for improved microbial control of water.

In some embodiments, heating or thermal activation of peracetate oxidant solutions to a temperature between about 38° C. to about 95° C. accelerates the formation of ROS daughter products as shown by greatly enhanced bleaching and biocidal activity with increasing temperature. Thermal activation that accelerates ROS production rate is useful for microbial control in heated environments and hot chemical sanitizing processes.

In some embodiments, a method is provided for reducing the microbial load in a slurry comprising containing a population of microbes with a peracetate oxidant solution; and mixing said slurry with the peracetate oxidant solution.

In some embodiments, the peracetate oxidant solutions are particularly suited for use in water with high salinity, alkalinity and contamination as they rely on reactive oxygen species whose performance is little impacted or enhanced by such conditions, in contrast to common Fenton and advanced oxidation processes that produce hydroxyl radical or ozonides as the primary ROS. The peracetate oxidant does not form bromate in bromide-containing water under typical treatment conditions, which is a benefit for treated water discharge. In some embodiments, the peracetate oxidant has a very low organic halide formation potential in wastewater treatment and pulp bleaching compared to chlorine and chlorine dioxide.

In some embodiments, the peracetate oxidant is generated at, or near, the point of use as an aqueous solution due to its high activity and relatively short half-life of minutes to hours depending on concentration and use conditions. The oxidant is active long enough to serve as a biocide before it attenuates leaving benign and readily degradable residuals including oxygen, sodium acetate and glycerol.

In some embodiments, the peracetate oxidant solution has low volatility because it is a solid in its native form and it forms a mildly alkaline solution. The peracetate oxidant solution can be significantly less corrosive in solution and the vapor phase than many common oxidants over a range of concentrations and temperatures. Low volatility is also a benefit for using peracetate oxidant in warm environments such as hot chemical sanitizing, cooling tower water loops, pulp bleaching and paper making.

In some embodiments, the contaminated water contains a population of microbes which may include slime forming bacteria, anaerobic sulfate reducing bacteria, anaerobic nitrate reducing bacteria, aerobic acid producing bacteria, iron related bacteria, fungi, molds, yeast, algae and microbes resistant to standard biocides.

BRIEF DESCRIPTION OF THE DRAWINGS

Advantages of the present invention may become apparent to those skilled in the art with the benefit of the following detailed description of the preferred embodiments and upon reference to the accompanying drawings.

Figure 1:
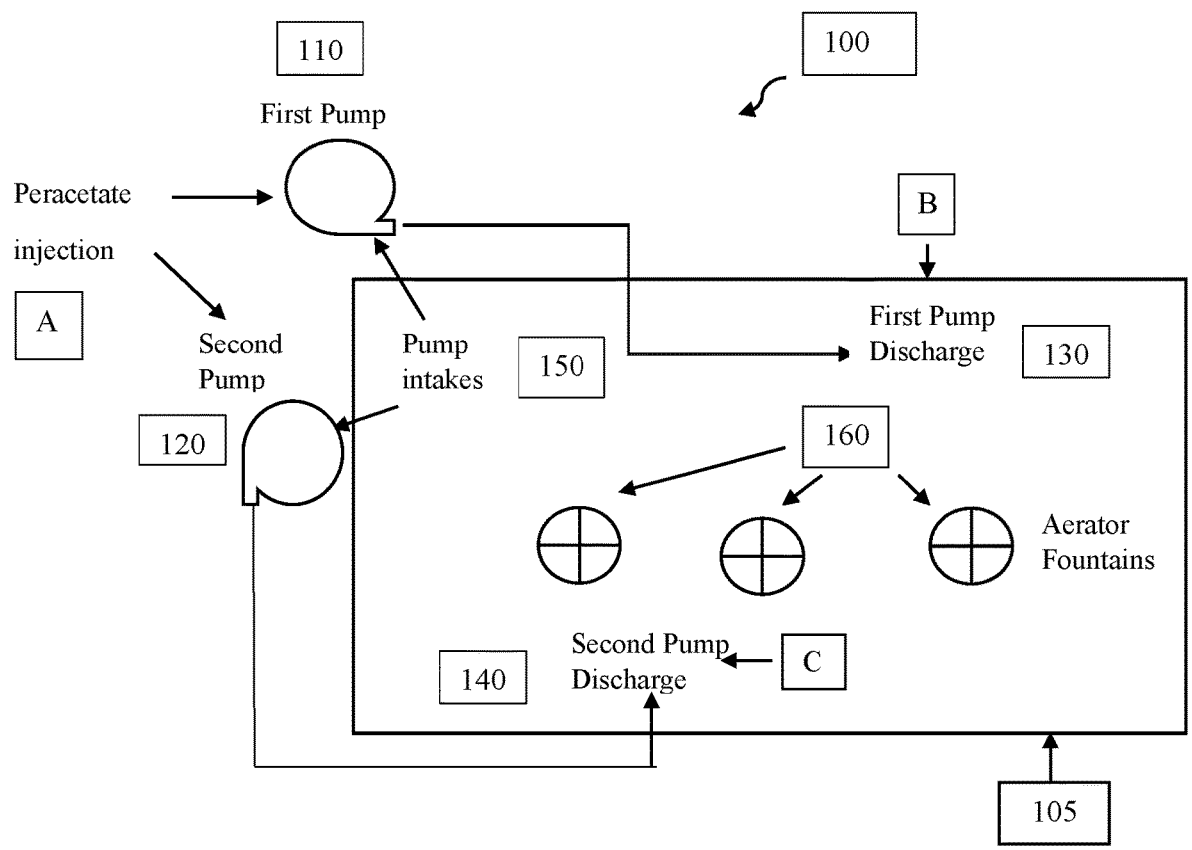
FIG. 1 is a simplified schematic diagram of an embodiment of a pond treatment processing system.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task. In some contexts, "configured to" may be a broad recitation of structure generally meaning "having a feature that" performs the task or tasks during operation. As such, the component can be configured to perform the task even when the component is not currently on.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "contaminated water" as used herein generally refers to water containing undesirable chemical or biological species that are to be at least in part removed by oxidative treatment including bacteria, other microorganisms, salt, scaling minerals, transition metals, dissolved and suspended inorganic materials, dissolved and suspended organic materials, oils, non-oxidizing biocides, scale inhibitors, iron stabilizers, hydrogen sulfide, and naturally occurring radioactive materials (NORM).

The term "reactive oxygen species" as used herein generally refers to a species such as may include singlet oxygen ($^1O_2$), superoxide radical ($O_2.^-$), hydroperoxyl radical (HOO.), hydroxyl radical (HO.), acyloxy radical (RC(O)—O.), and other activated or modified forms of ozone (e.g., ozonides and hydrogen trioxide). Each of these ROS has its own oxidation potential, reactivity/compatibility profile, compatibility/selectivity and half-life.

The term "reactive species oxidant" as used herein generally refers to oxidant formulations containing or capable of evolving at least one reactive oxygen species and can evolve at least one reactive carbon species. Such reactive species enhance the oxidative or reductive performance of the precursor formulation constituents.

The term "contaminated water source" as used herein generally refers to pipelines, tanks, and other equipment carrying raw waste water, greywater, ground water, tailing pond water, refinery waste water, oilfield produced water, various industrial and food processing waters, water recycling loops, pulp and paper mills, feedstock processing systems, cooling towers and water cooling loops, evaporation ponds and non-potable water systems.

The term "microbes" as used herein generally refers to aerobic and anaerobic bacteria (slime formers, acid producers, metal depositors, nitrobacteria, sulfate reducers, nitrate reducers), fungi, algae, molds, and yeast.

Embodiments

In some embodiments, oxidation chemistry may be used for microbial control of contaminated water, reducing biological growth, disinfecting and sanitizing. The oxidation chemistry used may have minimal impacts on pH and scaling potential of fluids. A relatively short-lived active oxidant may be a benefit for avoiding negative impacts on pulp quality, paper quality, fermentation feedstock quality, food product quality and for minimizing oxidant corrosivity and environmental impacts. Selectivity of the oxidation chemistry towards different materials is also desirable for efficiency of oxidant use, compatibility with a variety of materials and avoidance of unnecessary or undesirable side reactions. Oxidant solutions that generate a variety of reactive oxygen species (ROS) in their treatment environments may be good candidates for achieving some or all of these attributes.

ROS may be generated in-situ by several chemical methods including the Fenton catalytic cycle with hydrogen peroxide and iron catalysts (produces hydroxyl and superoxide radicals), combining ozone with hydrogen peroxide (produces ozonides and oxygen-based radicals), and combining hypochlorite with hydrogen peroxide (produces singlet oxygen). Other methods of generating ROS may include photochemical approaches, which are generally very dilute in ROS and are not practical for large volume treatment systems or for highly scaling fluids or fluids with high turbidity.

Some ROS (e.g., hydroxyl radical and ozonides) are too short lived and too reactive to be practical in highly contaminated or hydrocarbon environments. Salt and carbonate may rapidly quench the hydroxyl radical. Ozone and stronger oxidants, like hydroxyl radical, oxidize salts to form toxic chlorate and bromate byproducts. Chlorine-containing oxidant formulations are typically more corrosive than peroxides, are less efficient for $H_2S$ oxidation and rapidly chlorinate unsaturated hydrocarbons.

In some embodiments, a method provides for microbial control in water recycling loops, pulp and paper mills, cooling towers and water loops, feedstock processing systems, evaporation ponds and non-portable water systems. The methods may include providing a preferred ROS-producing oxidant formulation, peracetate oxidant solution.

In some embodiments, one preferred ROS-producing oxidant formulation is a peracetate solution. The peracetate solution may include generating an alkaline hydrogen peroxide solution from the combination of an alkali and a hydrogen peroxide concentrate, mixing the alkaline hydrogen peroxide solution with an acyl donor such that a peracetate solution concentrate is formed. In some embodiments, the peracetate solution may include peracetate anions and a peracid. In some embodiments, the peracetate solution may include a pH from about pH 10 to about pH 12. In some embodiments, the peracetate solution has a molar ratio of peracetate anions to peracid ranging from about 60:1 to about 6000:1. ROS-generating peracetate oxidant solutions may contain no hydrogen peroxide, and are produced on site and on demand at alkaline pH. The peracetate oxidant solution produces multiple ROS by itself and when placed into contaminated environments. In some embodiments, the ROS most important in peracetate oxidant solutions include singlet oxygen, superoxide radical, hydroperoxyl radical, acetyloxy radical and potentially other radical fragments. When a combination of these ROS are generated together in peracetate oxidant solutions they produce an oxidative-reductive potential (ORP) response in water that may exceed 900 mV (vs standard hydrogen electrode) around pH 7. These solutions may be more convenient and effective to use than other approaches. The dominant ROS may be selectively reactive such that they are effective in a variety of environments.

In some embodiments, a method may include making a reactive species formulation. The method may include providing an alkaline hydrogen peroxide solution. The method may include contacting the alkaline hydrogen peroxide solution with an acyl donor. A peracid concentrate may be produced by the contacting of the alkaline hydrogen peroxide with the acyl donor. The peracid concentrate may have a molar ratio of hydrogen peroxide to acyl donor reactive groups ranging from about 1:1.25 to about 1:4. The method may include maintaining the peracid concentrate pH value in a range from about pH 10 to about pH 12.

In some embodiments, a method of reducing the microbial load in contaminated water may include: providing a contaminated water containing a population of microbes and providing a peracid composition. The peracid composition may include a mixture of an alkali concentrate, a hydrogen peroxide and an acyl donor having a pH value ranging from about pH 10 to about pH 12. The peracid composition may include a first molar ratio of peracid anion to peracid acid ranging from about 60:1 to 6000:1. The peracid composition may include a second molar ratio of peracetate to hydrogen peroxide of 16:1 or more. The method may include contacting the peracid composition with the contaminated water. In some embodiments, the method may include mixing, after the contacting of the peracid composition and the contaminated water.

In some embodiments, a method reducing the microbial load in contaminated water further comprises separating the population of microbes from the contaminated water may include: providing a contaminated water containing a population of microbes and providing a peracid composition. The peracid composition may include a mixture of an alkali concentrate, a hydrogen peroxide and an acyl donor having a pH value ranging from about pH 10 to about pH 12. The peracid composition may include a first molar ratio of peracid anion to peracid acid ranging from about 60:1 to 6000:1. The peracid composition may include a second molar ratio of peracetate to hydrogen peroxide of 16:1 or more. The method may include contacting the peracid composition with the contaminated water. In some embodiments, the method may include mixing, after the contacting of the peracid composition and the contaminated water. In some embodiments, the method may include separating, after the contacting of the peracid composition and the mixing of contaminated water containing a population of microbes, into one of microbes and one of water.

In some embodiments, a method reducing the microbial load in contaminated water further comprises a method of separating the population of microbes and contaminated water containing impurities may include: providing a contaminated water containing a population of microbes and providing a peracid composition. The peracid composition may include a mixture of an alkali concentrate, a hydrogen peroxide and an acyl donor having a pH value ranging from about pH 10 to about pH 12. The peracid composition may include a first molar ratio of peracid anion to peracid acid ranging from about 60:1 to 6000:1. The peracid composition may include a second molar ratio of peracetate to hydrogen peroxide of 16:1 or more. The method may include contacting the peracid composition with the contaminated water. In some embodiments, the method may include mixing, after the contacting of the peracid composition and the contaminated water. In some embodiments, the method may include separating, after the contacting of the peracid composition and the mixing of contaminated water containing a population of microbes, into one of microbes, impurities and one of water.

In some embodiments, a method reducing the microbial load in contaminated water further comprises a method of heating contaminated water in a range from about 38° C. to about 95° C. prior to or following contacting with a peracid composition. Thermal activation that accelerates ROS production rate is useful for microbial control in heated environments and hot chemical sanitizing processes. Peracetate oxidant is more effective for microbial control in alkaline water than chlorine bleach and peracetic acid. Peracetate oxidant solution can be thermally activated to enhance its production of ROS and biocidal activity. Thermal activation is useful for microbial control in warm and hot water environments such as cooling water loops, pulp and paper making processes, down-hole oil and gas well treatments, hot chemical sanitizing (including clean-in-place applications) and pasteurization. For example, pulp bleaching is very slow at room temperature (takes more than 1 hour to achieve modest bleaching) but is very rapid at 50° C. (30 minutes to achieve significant bleaching).

In some embodiments, a method of reducing the microbial load in a slurry may include: providing a slurry containing a population of microbes and providing a peracid composition. The peracid composition may include a mixture of an alkali concentrate, a hydrogen peroxide and an acyl donor having a pH value ranging from about pH 10 to about pH 12. The peracid composition may include a first molar ratio of peracid anion to peracid acid ranging from about 60:1 to 6000:1. The peracid composition may include a second molar ratio of peracetate to hydrogen peroxide of 16:1 or more. The method may include contacting the peracid composition with the slurry. In some embodiments, the method may include mixing, after the contacting of the peracid composition and the slurry.

In some embodiments, a slurry for reducing the microbial load is selected from slurries of wood pulp and wood products, silica, polymers, polysaccharide gels, biomass feedstocks for fermentation, recycled paper and textiles and materials processed as slurries.

In some embodiments, the peracetate oxidant solution is shown to reduce toxic organic halide formation (e.g., chlorinated phenols, dioxins, haloacetic acids) during the bleaching of wood pulp and other fibers used in paper, packaging and molded fiber products including bamboo, eucalyptus, wheat straw, rice and other plant-based sources. For example, bleaching softwood pulp with the peracetate oxidant produces about ten times less total organic halides (TOX) than chlorine dioxide and about 2.5 times less TOX than peracetic acid. Bleaching with the peracetate oxidant can reduce pollution from chemical bleaching of fibers and minimizes toxic byproduct content in chemically bleached paper and molded fiber products such as those used for food packaging and compostable products.

The ability to mitigate microbes that have developed resistance to biocides is a growing challenge. Changing the biocide type periodically is one method used to mitigate microbes that have developed resistance to a particular biocide. This approach is often used in managing microbial populations in cooling tower water and other industrial water applications. However, resistance to multiple forms of chlorine and bromine has created problems with virulent pathogens that are increasingly resistant to antibiotics.

The peracetate oxidant solution provides several different oxidant species in a single solution including the peracetate parent oxidant and several daughter products formed in-situ including singlet oxygen, hydroperoxyl radical, superoxide radical and combined forms that impart high oxidative-reductive potentials (ORP) that are desirable for and correlated with effective microbial control. The combination of multiple oxidant species along with a high ORP can help mitigate resistance of microbes to disinfectants.

The presence of ROS or other reactive species in the formulations herein may in some cases be directly detected and it may be possible to determine the concentrations of certain reactive species (e.g., using spectroscopic methods). However, in some embodiments, in formulations herein the presence of reactive species may only be indirectly demonstrated by measurement of changing properties of the formulation (e.g., ORP measurements or pH change), by changes in concentration of precursors (e.g., rate of peroxyacetic acid concentration decline) or by changes in reactivity of the formulation (e.g., the rate of oxidation of dyes (bleaching rate)) or the rate or occurrence of oxidation of certain species (e.g., polysaccharide breakdown).

The oxidative reductive potential (ORP) is a measure of how oxidizing or reducing a solution is relative to a standard reference potential measured in volts. Standard reference potentials are measured relative to the hydrogen/hydrogen ion reduction-oxidation potential of 0.000 V at unit activity for the standard hydrogen electrode (SHE). Generally, solutions with potentials greater than 0 V vs SHE are considered oxidizing (electron accepting) while solutions with potentials less than 0 V vs SHE are considered reducing (electron donating). The measured ORP of water is influenced by its pH or hydrogen ion activity. As the hydrogen ion activity (e.g., concentration, temperature) increases, the ORP of water increases to more positive values. ORP is also influenced by the presence of reducing or oxidizing agents relative to their standard reduction-oxidation potentials and solution activities.

Standard oxidation potentials are often cited to compare the oxidative strength of oxidants. The standard potential is a thermodynamic value which is always greater than the measured ORP in solution for a given oxidant. This difference is caused in part by kinetic factors, such as the over potential or activation barrier of electron transfer at an electrode surface and the solution activity of the oxidant, which is proportional to the concentration. As a result, the standard potential is not a reliable measure of the chemical reactivity or antimicrobial activity of an oxidant regarding its reaction rate or reaction mechanism with a substrate. In contrast, a solution's ORP can be correlated with the level of microbial control for a given oxidant by measuring the reduction in microbial content achieved at that ORP in a given environment.

For example, according to the standard potentials hydrogen peroxide is a stronger oxidant than hypochlorous acid. However, the ORP of hypochlorous acid (29 mM) at pH 7 is over 1.1 V (vs SHE) while the ORP of hydrogen peroxide (29 mM) at pH 7 is about 0.5 V (vs SHE) indicating that hypochlorous acid is the stronger oxidant and biocide. Free radicals of chlorine are strong electron acceptors and also rapidly attack and substitute unsaturated and aromatic hydrocarbons, amines, thiols, aldehydes, ketones, and biological materials such as DNA and proteins. Hydrogen peroxide is a strong electron acceptor, but it is not a free radical, is less chemically reactive and exhibits lower antimicrobial activity than chlorine. This difference in chemical reactivity is reflected in the ORP. In practice, chlorine is used as a broad-spectrum biocide in water treatment whereas hydrogen peroxide is not.

ORP is used as a general measure of the antimicrobial strength of a solution containing an oxidizing antimicrobial agent, biocide or disinfectant. ORP may be correlated to relative oxidant concentration for lower oxidant concentrations at constant pH and temperature. This feature is the basis for ORP monitoring systems sometimes used in water treatment and disinfection processes where oxidant dose may be adjusted to maintain a desired ORP and corresponding biocidal activity for a particular oxidant.

Water solutions containing oxidizing biocides which have ORP's of greater than about 650 mV (vs SHE) are generally considered to be suitable for disinfection (Suslow, T. "Oxidation-Reduction Potential (ORP) for Water Disinfection Monitoring, Control, and Documentation" Univ. California Publication 8149 http://anrcatalog.ucdavis.edu which is incorporated by reference as if fully set forth herein) while ORP's above about 800 mV (vs SHE) are suitable for sterilization. Below about 475 mV (vs SHE) there is typically little to no biocidal activity for oxidizing biocides even after long contact times. Known exceptions to these ORP benchmarks include in-situ generation of short-lived reactive oxygen species such as hydroxyl radical, by ultraviolet-activated hydrogen peroxide, or singlet oxygen, by dye-sensitized photo-activation of molecular oxygen. Although the peracetate oxidant solution produces short-lived ROS, the combination of ROS and the parent peracetate oxidant create a metastable complex or a new species which exhibits an elevated solution ORP which can be correlated with effective microbial control.

There are several limitations to ORP measurement as a method for evaluating antimicrobial activity. ORP is normally not sensitive to very short-lived reactive oxygen species such as hydroxyl radicals, singlet oxygen, hydrogen trioxide and hydroperoxide radical in the presence of parent oxidants such as, for example, hydrogen peroxide, peroxyacetic acid, molecular oxygen and ozone. ORP is not sensitive to non-oxidizing biocides and chemical reactivity which impart other mechanisms for disrupting cellular viability. Examples of non-oxidizing chemical biocides include glutaraldehyde, which acts by crosslinking protein structures, and antimicrobial quaternary ammonium compounds, which disrupt cell membranes. ORP is also insensitive to the tolerance of various microorganisms to a given biocide, which affects the concentration and contact time required to inactivate or destroy a specific microorganism. For example, chlorine use in water treatment is not effective against certain spores (e.g., *Cryptosporidium oocysts*) while chlorine dioxide and ozone are.

In some embodiments, methods of oxidation employ reactive oxygen species formulations as described herein. The oxidation method includes application of one or more selected reactive oxygen species formulations to an environment, a substrate in an environment or to a substrate that is to be subjected to oxidization. The terms environment and substrate are used herein broadly to refer to a place, a material, a chemical and/or a biological species that is to be subject to at least partial oxidation. The environment may be, among others, water in situ, for example, pipelines, tanks, and other equipment carrying raw waste water, greywater, ground water, tailing pond water, refinery waste water, oilfield produced water, various industrial and food processing waters, water recycling loops, pulp and paper mills, cooling towers and water loops, evaporation ponds and non-potable water systems. A substrate may be any item or place that are to be oxidatively cleaned for example, containers, tanks, pipes, counter tops, appliances, food preparation surfaces and equipment, food and beverage containers, filters, food items during food processing, that are subjected to oxidative cleaning.

In specific embodiments, the environment is contaminated water containing undesirable chemical or biological species that are to be at least in part removed by oxidative treatment. Water to be treated includes waste water, greywater, raw water, ground water, tailing pond water, refinery waste water, produced water, various industrial and food processing waters, water recycling loops, pulp and paper mills, cooling towers and water loops, evaporation ponds, feedstock process systems and non-potable water systems. In an embodiment, the environment or substrate is contaminated with higher than desirable levels of microorganisms wherein the environment or substrate is to be disinfected. The reactive oxygen species formulations may be used as antimicrobial agents, disinfectants and biocides. For example, the formulations may be used for cleaning and disinfection of medical or dental equipment, food processing equipment, containers and surfaces.

In some embodiments, the formulations may be used in various applications as oxidants and/or biocides. As described herein, different formulations, as assessed by ORP measurement and dye oxidation rate among other properties, may exhibit enhanced activity as a chemical oxidant or as a disinfectant, antimicrobial or biocide.

In some embodiments, uses of the reactive oxygen species formulations are provided herein for various industrial or domestic oxidation, clean up and disinfection applications. More specific applications include without limitation, water treatment and reuse; produced water treatment, process water cleaning and reuse, waste water treatment, greywater, raw water, ground water, tailing pond water, refinery waste water, cooling tower cleaning, cleaning/disinfections of water wells, pipes and containers, textile dye recycle and waste water treatment, pulp and paper processing waste water treatment and recycle, specialty bleaching applications, evaporation ponds and non-potable water systems.

Reactive oxygen species formulations may be employed as an antimicrobial agent or oxidizing agent for treatment of water, including without limitation, process streams or waste streams. Reactive oxygen species formulations may be used in water treatment: to cause chemical transformation or degradation of components or contaminants; to promote or enhance flocculation, micro-flocculation, coagulation and subsequent clarification and separation of inorganic and organic materials; to promote or enhance biological treatment processes; to promote or enhance wet peroxide oxidation processes; as a pretreatment, intermediary treatment or post treatment process to other treatment and separation processes.

In water treatment processes, the chlorine-free and bromine-free reactive oxygen species formulations may be used to provide treatment without formation of undesired chlorinated or brominated byproducts. In water treatment processes, the chlorine-free and bromine-free active oxygen species formulations may be used to provide treatment in the absence of chlorine, chlorine dioxide and/or ozone.

For applications of the formulations herein the formulation is contacted with a substrate or environment to be oxidized or treated. Any means of contacting may be employed, that is suitable for retention of the oxidation activity of the formulation and that is suitable for the environment and/or substrate. Formulations are liquid and may be employed in a concentrated form or a diluted form. Formulations may be diluted, if desired, before, during or after initial contact. The concentration of formulations in contact with an environment and/or substrate may be varied during contact.

A given application may employ separate contacting events which may be the same or different and which may employ the same formulation or precursor formulation. A given application may employ contact with more than one formulation or precursor thereof. The environment and/or substrate may, for example, be contacted with an activated liquid formulation containing reactive oxygen species. Alternatively, the environment and/or substrate may be contacted with a liquid precursor formulation that will generate reactive oxygen species on activation and the formulation is activated as or after it comes into contact with the environment or substrate.

For example, the environment or substrate may itself provide for activation, such as providing acidity that affects ROS formation rates and changes in oxidant speciation, fragmentation behavior or reactivity caused by acid-base equilibria. One or more additional steps of activation to form additional reactive species may occur after the contact of the formulation or the precursor formulation with the environment and/or substrate. For example, redox active materials or charged materials including transition metal species, unsaturated organic materials, sulfides and suspended solids can interact with and react with the parent oxidant to initiate fragmentation of the parent peracetate oxidant leading to the formation of ROS. Thermal activation can also be used to increase the formation rate of ROS, increase the fragmentation rate of the peracetate and increase overall peracetate oxidant solution's antimicrobial activity, bleaching power and reactivity with impurities or substrates. Irradiation of peracetate-containing solutions with ultraviolet light may also be used to promote activation. Contact with the environment or substrate may be controlled by addition of a selected volume or concentration of formulation or its precursor to the environment or in contact with the substrate. Alternatively, contact may occur by addition, including controlled addition of the substrate to the formulation or a precursor thereof.

Contact may be combined with stirring or other agitation, with scrubbing, scraping or other abrasive method if appropriate for the environment and/or substrate. Contact may be combined with removal precipitant or other solids present or formed in the environment or on contact with the substrate. The environment or substrate may be pre-treated prior to contact. The treated environment to substrate may be subject to another form of cleaning or disinfection.

Water system equipment is serviced to remove bacterial growth, biofilm, slime buildup, mineral scale deposits, corrosion and contamination. These issues are common among, waste water, greywater, raw water, ground water, tailing pond water, refinery waste water, produced water, various industrial and food processing waters, water recycling loops, pulp and paper mills, cooling towers and water loops, evaporation ponds and non-potable water systems. Microbial control, removal of slime (the decaying remains of dead bacteria and other organic materials), microbial corrosion control and scale removal are significant maintenance issues for prolonging the production capacity and lifetime these systems. Pipelines, tanks and other equipment carrying raw water, wastewater, produced water, greywater and other untreated water will encounter microbial growth and slime formation and will require cleaning.

Microbial control in water is imperative to a wide variety of processing and manufacturing systems. These systems can include water recycling loops, pulp and paper mills, cooling towers and water loops, evaporation ponds and non-potable water systems. Treatment of water for microbial control in water recycle loops is critical for maintaining efficient processes, protecting equipment from biofouling and biocorrosion, preventing contamination of products, reducing downtime and protecting the health of people exposed to such processes and products. Furthermore, microbial control in water recycle loops also provides odor control by minimizing fermentation, hydrogen sulfide production and algal decomposition. Microbial control in pulp and paper mills serves to protect the integrity of pulp slurries, coating ingredients, whitewater loop, process equipment, and paper quality. Controlling sessile bacteria helps to prevent the accumulation of biofilm deposits which cause microbiologically influenced corrosion (i.e., biocorrosion). Slime deposits are often a combination of bacteria and fungi. Importantly, when biofilms and their detritus detach from surfaces in the wet end papermaking process, they can cause holes and other defects in finished paper products. Therefore, preventing biofilm growth helps to avoid such defects. Microbial control in cooling towers and cooling water loops serves to improve cooling efficiency, minimize microbiologically influenced corrosion, control odors, prevent clogging of pumps and pipes, reduce microbial loading in blowdown, and minimize microbial exposure of surrounding areas from drift. Microbial control may also occur on surfaces serving to bleach, sanitize and/or disinfect the surfaces of a processing or manufacturing system. Microbial control targets include aerobic and anaerobic bacteria (slime formers, acid producers, metal depositors, nitrobacteria, sulfate reducers, nitrate reducers), fungi, algae, molds, and yeast. Some bacteria are pathogenic, for example, *Legionella pneumophila*, which poses health risks. Some algae, such as cyanobacteria, produce algal toxins that pose potential health hazards.

Biocides used for microbial control need to be effective and efficient at neutral and alkaline pH. They also need to be effective at elevated levels of suspended solids (including silt, pulp, fillers, pigments, suspended metals, oils, polymers) and dissolved solids (including salt, scaling minerals, carbonate, dissolved metals, scale inhibitors and other additives that may be encountered in various processes). Oxidizing biocides are a fast-acting line of defense and represent a significant expense in operations. Oxidizing biocides should be very active and have a limited lifetime with no reactive residuals so that they do not interfere with non-oxidizing biocide chemicals used to provide longer-term biostatic conditions.

Referring now to an exemplary water treatment processing system 100 as shown in FIG. 1 for illustrative purposes only, a typical chlorine bleach treatment is conducted by adding 12.5% bleach solution rapidly into one end of the pond 105 (each 2100 gallons in about 15 minutes) where pump intakes 150 are located. The first pump 110 and second pump 120 are used to distribute the bleach plume and mix the pond water column during treatment. A first pump 110 circulates water at a rate of up to 4200 gallons per minute with its discharge pipe 130 extending to near the opposite end of the pond. A second pump 120 circulates water at a rate of up to 1800 gallons per minute with its discharge pipe 140 extending to about half way to the opposite end of the pond. The pump discharges are arranged to circulate the water in a clockwise direction around the pond. Water pumping and circulation is conducted for 2-4 hours following bleach addition. In some embodiments, the pond had three modest-sized aerator fountains 160 that were operated up to 12 hours per day.

Compounds for microbial control in system 100 can be injected at multiple points throughout the system. Exemplary, but by no means limiting injection points illustrated in FIG. 1 include:

Injection point A: in suction side of first pump or second pump;

Injection point B: in first pump discharge; and

Injection point C: in second pump discharge.

In one embodiment, peracetate oxidant solution is added to at least one of the injections points A, B, and C. at injection. The peracetate oxidant solution could replace or be used in conjunction with chlorine bleach or other common bleaching compounds. Peracetate oxidant injection at Injection point A results in improved efficiency of oxidant mixing, contact and water treatment.

An alternative is to use injection points B and C.

Another embodiment is the ability to combine the use of peracetate oxidant solution and chlorine bleach for improved antimicrobial treatment of water. When a highly impaired water is treated with peracetate oxidant solution the ORP can be increased to, for example, about 600-700 mV vs SHE, which is a reasonable level for microbial disinfection. Treating the same water with a comparable dose of bleach can increase the ORP to a similar mV range, which is also a reasonable level for disinfection. When the bleach treatment is added on top of the peracetate oxidant treatment the ORP can be increased to over 800 mV, which indicates that there is an additive oxidative effect that increases the oxidation potential of the water and the corresponding level of antimicrobial treatment. This additive behavior between oxidants is in contrast to the typical consumptive reaction between peroxide-based oxidants and chlorine bleach. For example, combining hydrogen peroxide treatment with chlorine bleach treatment results in the consumptive reaction between bleach and hydrogen peroxide and a net loss of oxidants.

Similarly, combining peracetic acid treatment with chlorine bleach treatment results in reaction between bleach and the hydrogen peroxide contained in the peracetic acid solution (e.g., 15% peracetic acid solution can contain 10-25% hydrogen peroxide) resulting in a net loss of oxidants. In addition, the alkalinity of chlorine bleach (sodium hypochlorite in sodium hydroxide solution) can accelerate the consumptive reaction between peracetic acid and hydrogen peroxide when diluted into a water stream of neutral to slightly alkaline pH (peracetic acid is ionized by alkalinity and then reacts with hydrogen peroxide).

In some embodiments, peracetate oxidant solution showed an unexpected, rapid thermal activation behavior at pH 8.5 and 50° C. in clean water conditions. To test this behavior without competing contributions from impurities the peracetate oxidant concentrate was added to distilled water pre-heated to 50° C. After the solution pH naturally decreased from 10 to 8.5 it was maintained at pH 8.5 throughout the remainder of the test by adding 4 M sodium hydroxide as needed. The concentration of peracetate oxidant decreased over time with an accompanying increase in ORP to over 700 mV vs SHE within 40 minutes. The decrease in peracetate concentration and increase in ORP was significantly faster at 50° C. than that previously observed at room temperature in clean water conditions. The peracetate consumption and ORP behavior suggests that one or more intermolecular reactions is occurring between molecules and/or reactive oxygen species generated in-situ at the expense of peracetate. The products of these reactions generate a composition with meta-stable species that exhibit a high ORP. In contrast, the same test with peracetic acid showed stable peracetic acid and hydrogen peroxide concentrations for about 90 minutes and the ORP was constant around 280 mV vs SHE.

In some embodiments, microbial control in water at slightly alkaline pH was compared between peracetate oxidant, chlorine bleach, peracetic acid and chlorine dioxide Alkaline pH is encountered in a variety of applications where microbial control and sanitization is needed, including pulp and paper processing, cooling towers, water treatment and chill tanks in poultry processing. Some oxidants are less effective at sanitizing at alkaline pH such as chlorine bleach (hypochlorite) at a pH above its pKa of 7.5. Peracetate oxidant and chlorine dioxide performed well as antimicrobial disinfectants at slightly alkaline pH compared to peracetic acid and chlorine bleach, which had the lowest performance.

Figure 2:
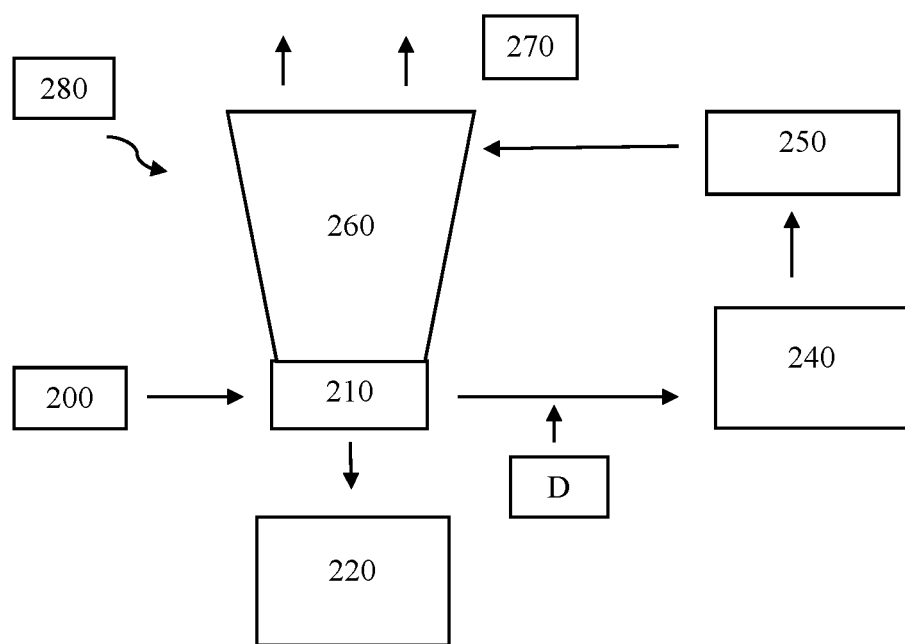
FIG. 2 is a simplified schematic diagram of an embodiment of a cooling tower processing system.

Referring now to an exemplary cooling tower treatment processing system 280 as shown in FIG. 2 for illustrative purposes only, a typical chlorine bleach treatment is conducted. Makeup water 200, such as municipal water, river water, pond water, ground water or reclaimed water is fed into the Basin 210 of a cooling tower to make up for the amount of water lost to evaporation, drift and Blowdown 220. Blowdown 220 is removed from the Basin 210 of the cooling tower to remove water as it becomes more concentrated in salt, scaling minerals, microbes and other chemicals and impurities. Addition of chlorine bleach for microbial control can be made on the suction side of the water circulation pump 240 to provide uniform mixing and minimize oxidant loss to Blowdown. The bleach containing cooling water flows through the Heat Exchanger 250 where the water absorbs heat. The heated water flows to the evaporative cooling tower 260 where air is blown or drawn through a cascade or spray of the heated water. The evaporation process cools the water before it returns to the Basin 210. During the evaporation process water mist or aerosol can escape the cooling tower, known as Drift 270. The Drift 270 is composed of water containing dissolved and suspended solids, chemicals and microbes.

Compounds for microbial control in system 280 can be injected at multiple points throughout the system. Exemplary, but by no means limiting injection points illustrated in FIG. 2 include:

Injection point D: on the suction side of the water circulation pump.

In one embodiment, peracetate oxidant solution is added to injection point D at injection. The peracetate oxidant solution could replace, be used in conjunction with or used following chlorine bleach or other common bleaching compounds. Peracetate oxidant injection at Injection point D results in improved efficiency of oxidant mixing, contact and water treatment.

Another embodiment is the ability to shock-treat a cooling tower following treatment with chlorine bleach for improved microbial control of water. For example, an evaporative cooling tower at a municipal power plant is on a chlorine treatment program for microbiological control, the makeup water source is primarily river water containing some alkalinity, resulting in a slightly alkaline pH about 7.8-8.2 in the cooling tower. The total oxidant concentration in the cooling water is maintained around 0.2 to 0.5 ppm $Cl_2$ to minimize corrosion rate and chemical costs. At this chlorine concentration and pH the ORP of the cooling water is around 500-575 mV (vs SHE), a range correlated with biostatic conditions, but less than that needed for disinfection. Over time the microbial load in the water and on surfaces of the condenser can increase leading to lower heat exchange and cooling efficiency and increased microbial corrosion. The microbial population can also develop a tolerance to chlorine. Increasing exposure risk to microbes in the drift, such as *legionella*, is also a concern.

In an embodiment, a cooling tower was shock-treated with peracetate oxidant solution to reduce the sessile microbial load at the condenser and to reduce the overall bacteria population (planktonic and sessile) in the cooling tower water circulation system and basin. Shock treatment with elevated concentrations of peracetate oxidant is enabled by its low corrosivity, high biocidal activity and ORP at alkaline conditions and enhanced biocidal activity when thermally activated at the condenser (water temperature at the condenser can reach 130-160° F.).

A two hour treatment with peracetate oxidant solution elevates the oxidant concentration to about 20 ppm at the condenser where it is thermally activated for microbial reduction in the water and biofilm disruption, but has a corrosion rate less than 1 mpy on copper and other sensitive metallurgy even though the ORP is elevated up to as high as 750 mV (vs SHE). The residual oxidant concentration in the water returning to the basin is approximately 10 ppm, which provides bacteria control and reduction throughout the water circulation system. Sequential dosing of additional peracetate solution on top of a 10 ppm residual in a recirculation loop also provides a synergistic antimicrobial performance improvement over just a single oxidant spike.

Figure 3:
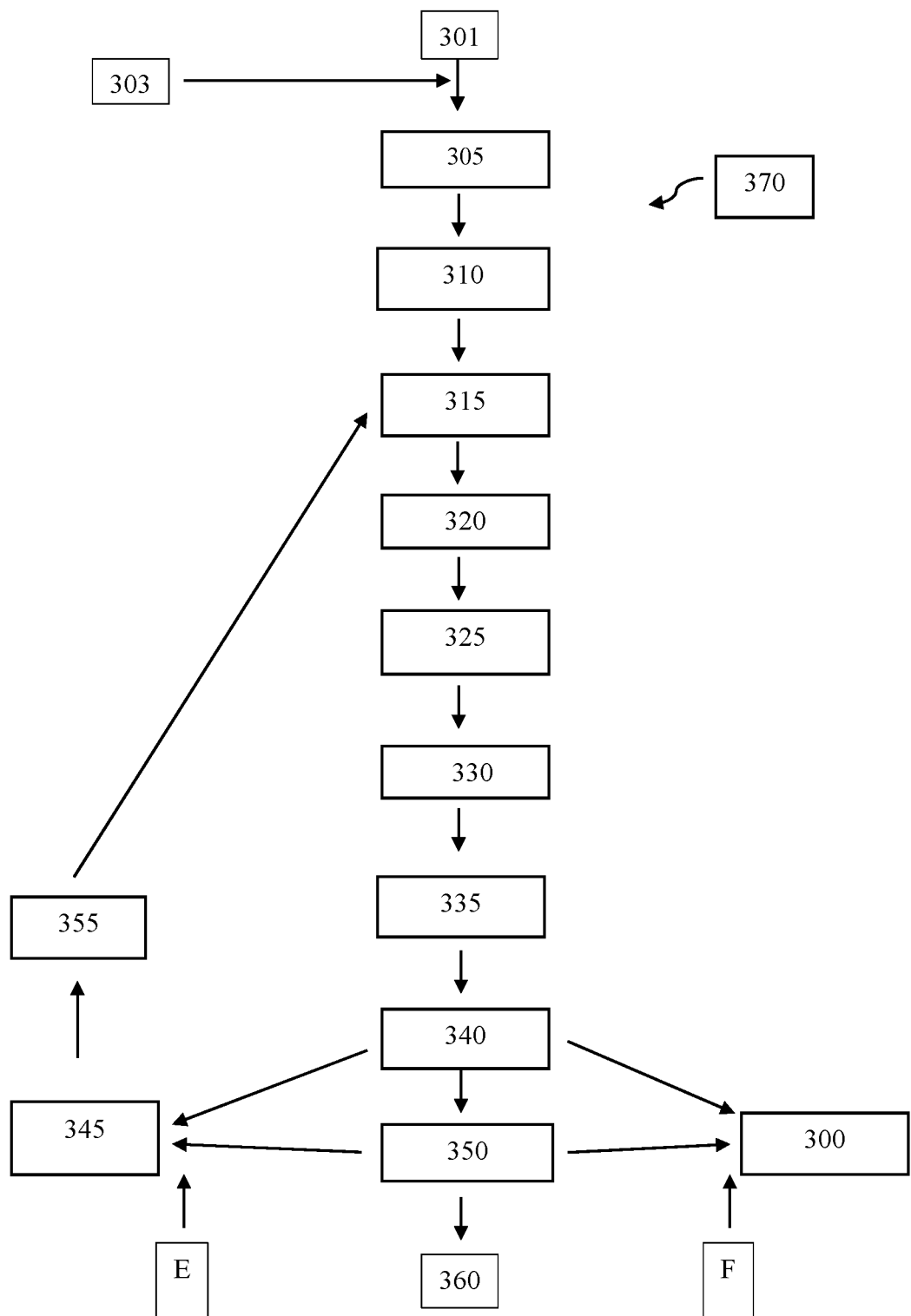
FIG. 3 is a simplified schematic diagram of an embodiment of a pulp and paper processing system.

Referring now to an exemplary paper mill processing system 370 as shown in FIG. 3 for illustrative purposes only, typically chlorine bleach is used to control microbial growth in printing paper in stock preparation and white water recovery. Pulp stock or fiber furnish 301 is pumped into the blend chest 305 where chemical additives 303 may be added, such as dyes. A blend of pulp types (hardwood and softwood) may be added and combined. Re-processed fiber and broke pumped from the broke chest 300 are also combined in the blend chest 305. The thick stock made in the blend chest 305 is transferred to the machine chest 310 where the consistency is leveled during a short retention time. The thick stock is then transferred to the wire pit 315 for dilution to the head box consistency. The diluted stock then passes through a cleaner bank 320 to remove unwanted solids and then to a deaerator 325 to separate entrained gas from the stock. After passing through a final screening 330 the diluted stock is fed into the head box 335. From the head box 335 the stock is fed to the former or wires 340 for sheet forming. Suction boxes under the wire remove bulk water from the sheet and this water is sent to the white water chest 345. The sheet then passes through a series of heated drying rollers and pressing rollers to produce the finished paper sheet 360. The white water is sent through a cleaning device 355, such as a centrifuge, to separate and recover fibers before the water returns to the wire pit 315 for stock dilution. Trimmings and loose fiber are collected from the former 340, pressing and drying 350 stages and sent to the broke chest 300. The broke is processed into dispersed fiber and returned to the blend chest 300. Each stage in the paper mill, and every surface in that stage, is contaminated with microbes and requires periodic cleaning to maintain consistent paper quality. Two locations for chlorine bleach addition for microbial control in the white water 345 and broke chests 300 are shown.

Compounds for microbial control in system 370 can be injected at multiple points throughout the system. Exemplary, but by no means limiting injection points illustrated in FIG. 3 include:

Injection point E: at the white water chest; and

Injection point F: at the broke chest.

In one embodiment, peracetate oxidant solution is added to at least one of the injection points E and F at injection. The peracetate oxidant solution could replace or be used in conjunction with chlorine bleach or other common bleaching compounds. Peracetate oxidant injection at Injection points E and F results in improved efficiency of oxidant mixing, contact and water treatment.

In some embodiments, sodium peracetate oxidant solution is used to control microbial growth in a printing paper mill in stock preparation and white water recovery. White water entrains fiber, chemicals and microbes from the paper web. Microbes have an opportunity to propagate during extended residence time in the white water chest. Pulp sources entering the machine chest, such as boke and recovered fiber, will carry elevated microbial loads after their recovery form the paper machine process. Microbial concentrations can exceed $10^6$ to $10^7$ cells/mL, a level that reduces paper quality, accelerates biofilm growth and microbially influenced corrosion, increases paper defects and odor problems. These problems increase the frequency of down time for maintenance and increase paper reject.

Several points exist where the peracetate oxidant solution can be added to the paper mill process. Ideally the peracetate solution is added to a fluid (water and pulp) where there is a contact time of several minutes to allow for more effective microbial control in the presence of high solids and allowing for thermal activation of the peracetate in warm and hot water streams that are typical in a paper mill. The use of peracetate oxidant has virtually no impact on pH, thereby avoiding the use of a second chemical feed for pH balance as is necessary when using moderate concentrations of acidic oxidants like chlorine dioxide and peracetic acid in a closed or partially closed-loop system.

In some embodiments, the peracetate oxidant solution is shown to be efficient for the bleaching of Kraft pulp and its performance approaches that of chlorine dioxide. The preferred pH for bleaching with peracetate oxidant solution is about pH 8 to about pH 12 where the ROS content and activity is greatly enhanced at elevated temperatures. Pulp bleaching is very slow at room temperature (takes more than 1 hour to achieve modest bleaching) but is very rapid at 50° C. (30 minutes to achieve significant bleaching). For comparison, the most efficient pH for bleaching with peracetic acid is at pH 7 and lower, however it is not as efficient as peracetate oxidant overall and does not show thermal activation for the production of ROS. Using peracetate oxidant in pH neutral to alkaline bleaching conditions has very little impact on alkali consumption in the bleaching process. In contrast, pH neutral to alkaline bleaching with chlorine dioxide or peracetic acid consumes large quantities of alkali to neutralize the acidity in these oxidants as alkali is caustic soda.

In some embodiments, production of chemicals and fuels from bio-based, renewable feedstocks is achieved by fermentation or transformation with engineered microbes including yeasts, bacteria and enzymes. The engineered microbes can be rapidly contaminated and overwhelmed by wild strains present in the feedstock materials unless the feedstocks are disinfected prior to their addition to a fermenter or bioreactor. There are a wide variety of feedstocks being utilized in bio-based chemical production including, for example, natural polysaccharide materials (guar and xanthan gums, lignin), sugars (corn, cane, beet, sorghum, wheat and tapioca), fats, fatty acids, glycerin, corn stover, mechanically pulped trees and switchgrass. Feedstocks are often disinfected or sterilized under autoclave conditions, high pressure steam at 121° C., to avoid introducing chemistry that would degrade feedstock or product quality such as halogen-based oxidizing biocides and ozone. However, autoclave treatment has high energy and equipment costs and is an excessive microbial control method for chemical and fuel production.

Figure 4:
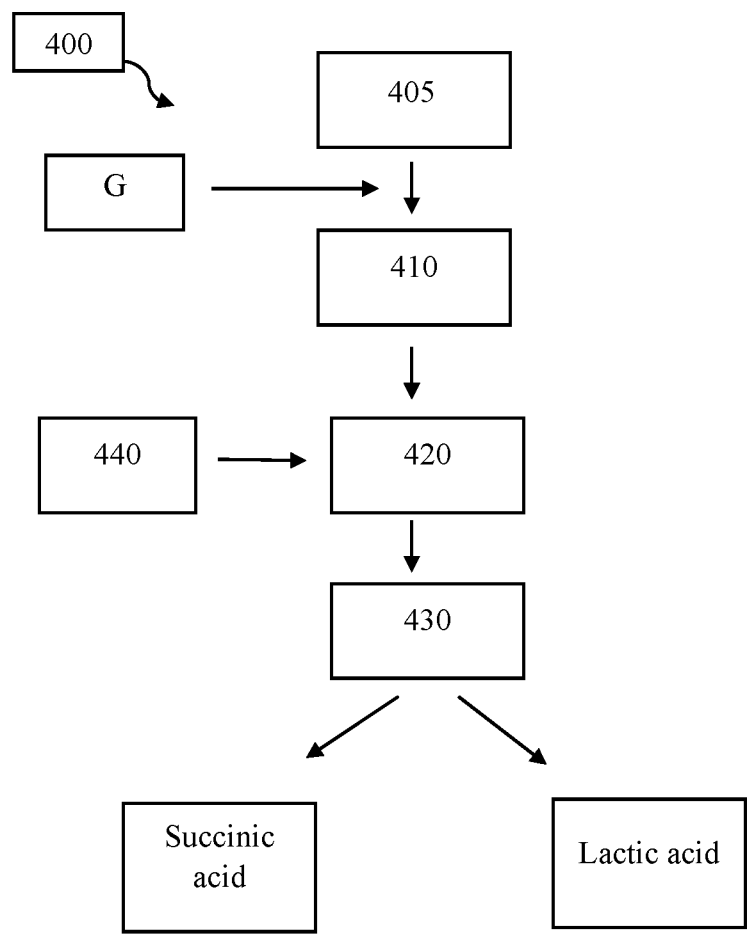
FIG. 4 is a simplified schematic diagram of an embodiment of a feedstock processing system.

Referring now to an exemplary feedstock processing system 400 as shown in FIG. 4 for illustrative purposes only using high pressure steam, feedstock material 405 is placed in a heated blending tank 410 and mixed, the material is then fed to a fermenter 420 along with nutrients, pH buffers or additives 440 necessary for fermentation process. Following fermentation chemical products 430 are recovered and are separated into succinic acid and lactic acid.

Compounds for microbial control in system 400 can be injected at multiple points throughout the system. Exemplary, but by no means limiting injection points illustrated in FIG. 4 include:

Injection point G: before the blending tank.

In one embodiment, peracetate oxidant solution is added to at least one of the injection point G at injection. The peracetate oxidant solution could replace or be used in conjunction with autoclave conditions.

In some embodiments, peracetate oxidant solution is used for microbial disinfection of polysaccharide feedstock materials used for producing succinic acid and lactic acid in a fermentation process. The peracetate is blended with the feedstock mixture in a blending tank to make an initial sodium peracetate concentration of up to about 130 ppm (by weight) and this mixture is heated to around its fermentation temperature of about 50-60° C. In this temperature range thermal activation of the peracetate oxidant occurs which increases antimicrobial activity and the rate of oxidant consumption such that the treatment is more rapidly finished and active oxidant is eliminated before entering the fermentation stage containing the engineered microbes.

For example, a guar gum dispersion in water was tested for microbial disinfection and preservation with sodium peracetate solution. Guar gum dispersions were made in 150 mL glass jars with air tight covers by dissolving/dispersing 0.60 grams of food grade guar gum in 60 mL of distilled water containing 0.60 g of sodium chloride to make 1% guar dispersions. The dispersions were heated in a water bath to 30° C. for 45 minutes to hydrate the guar. A first jar sample was cooled to room temperature and held as the control sample. The viscosity of the room temperature guar dispersion was similar to warm honey. A second jar sample was spiked with about 130 mg/L dose of sodium peracetate and mixed thoroughly. The temperature was maintained at 30° C. for 60 minutes and then cooled to room temperature. The viscosity of the second sample appeared very similar to the first. Within 24 hours of preparation the first, control sample had a significant loss of viscosity while the second, treated sample remained visibly unchanged. After seven days the first, control sample had microbial growth visible as a biofilm developing on the surface of the liquid while the second, treated sample remained visibly unchanged.

In some embodiments, peracetate oxidant solution is used for sanitization. The sanitization of equipment used for food, beverage and dairy processing and the sanitization of packaging, bottles and containers for packaging of these products is critical for protecting consumers from illness, prevent spoilage, increase shelf life, and maintain clean equipment and facilities. Common methods of sanitizing equipment surfaces is conducted by soaking, spraying and clean in place (CIP) processes. CIP processes involve the preparation of cleansers and sanitizer solutions in day tanks (often in 50-500 gallon volumes) and dispensing them into pipes, tanks and other processing equipment that is not disassembled for cleaning.

Chemical cleansers and sanitizers are used where hot water sanitization at high temperature (at least 77° C.) is not practical or damaging to equipment and where other contaminants (e.g., organic materials, mineral scale, stains) also need to be removed Alkaline oxidizing cleanser solutions are particularly effective at removing protein soils, oils, fat deposits and killing microbes compared to alkali detergents alone. Acidic oxidizing cleansers are effective at removing mineral scale, milkstone, iron and killing microbes.

The heating of sanitizing solutions (e.g., hypochlorite, chlorine dioxide, iodine, peracetic acid) to modest temperatures (typically 40-60° C.) is a common practice to improve the effectiveness of a disinfectant. This is partly based on the principles that diffusion rates and chemical reaction rates increase with increasing temperature and that surface tension decreases thereby improving surface wetting and interaction with microbial deposits. The peracetate oxidant solution has the additional benefit over conventional oxidizing biocides of being thermally activated to produce multiple germicidal reactive oxygen species more rapidly, which significantly accelerates and increases the oxidant solution's sanitizing power. The peracetate oxidant performs well at alkaline pH making it effective for alkaline oxidizing cleanser solutions with strong germicidal activity.

Hypochlorite is problematic in heated sanitizing solutions due to its corrosivity to stainless steel, particularly aggressive pit corrosion. For example, the warranty of a stainless steel cleanser system or CIP system is voided if the chlorine concentration exceeds 80 mg/L at 40° C. The presence of chloride ion also enhances the corrosion of stainless steel at elevated temperatures. Chlorine is also volatile and off-gasses rapidly from warm cleanser solutions.

Peracetate oxidant solution is compatible with stainless steel and has a very low corrosion rate on copper. It has low volatility allowing it to remain in solution at elevated temperatures for improved efficiency and eliminates exposure of personnel to chlorine or chlorine dioxide vapors. Peracetate oxidant has very low halogenated byproduct formation potential making it safer for cleaning and sanitizing food contact surfaces (no toxic halogenated residues) and preventing discharge of halogenated oxidation and disinfection byproducts. Because of these attributes peracetate oxidant can be safely used in higher concentrations than hypochlorite, chlorine dioxide and ozone for sanitization.

In some embodiments, transport and storage of peracetate oxidant solutions is avoided by its generation from stable feedstocks at or near the point of use. The small amount of peracetate present on site is produced in water at dilute concentrations (less than 8%) thereby avoiding hazards associated with highly concentrated or pure oxidant materials and minimizing fugitive air emissions and worker exposure to harmful materials, VOCs or nuisance odors. Potential fugitive air emissions from the peracetate oxidant solution production process are a small amount of water vapor and oxygen gas. The produced peracetate oxidant solution concentrate is dispensed by means of a pump, eductor or other engineered conveyance device that transfers the liquid product in a contained system to the point of use. The peracetate oxidant solution is produced as needed on site and on demand thereby eliminating storage and handling of large quantities of the oxidant product material on site.

In some embodiments, peracetate oxidant solutions have the ability to reduce corrosion in pulp and paper mills serving to protect the integrity of pulp slurries, coating ingredients, whitewater loop, broke processing system, process equipment, and paper quality. Controlling sessile bacteria helps to prevent the accumulation of biofilm deposits which cause microbiologically influenced corrosion (i.e., biocorrosion). Slime deposits are often a combination of bacteria and fungi. Importantly, when biofilms and their detritus detach from surfaces in the wet end papermaking process, they can cause holes and other defects in finished paper products. Therefore, preventing biofilm growth helps to avoid such defects.

In some embodiments, peracetate oxidant solution is less corrosive than commonly used oxidizing biocides (chlorine, chlorine dioxide), especially when the biocides come in contact with various process materials such as steel, copper and brass alloys. Oxidizing biocides used in processes where elevated temperatures and turbulence are present in the liquid phase should ideally have low vapor pressures to minimize oxidant loss to evaporation and vapor phase corrosion of surrounding equipment and structures. It is important to consider corrosion rates of materials like metal alloys under various oxidant use conditions including shock treatments and bleaching at high concentrations, water treatment at lower concentrations and vapor corrosion in the head space above oxidant solutions.

In some embodiments, corrosion conditions evaluated were relevant to shock treatment in pipes and well casings. Steel alloy was tested as a common pipe and well casing steel with resistance to hydrogen sulfide corrosion and is used in the oilfield. Copper coupons were tested as a common material used in heat exchangers in cooling towers and water cooling loops. Side-by-side corrosion tests using different oxidants (peracetate oxidant solution, chlorine dioxide and chlorine bleach) under the same test conditions demonstrated significantly reduced corrosion rates for the peracetate solutions compared to the other oxidants tested. Shock treatment corrosion tests were conducted over a period of 24 hours without replenishing oxidant. These conditions were conducted to simulate a single, elevated oxidant dose applied in a shock treatment program. The duration of the shock treatment is expected to be limited in time by the rate of oxidant consumption, which is expected to be less than 24 hours in highly contaminated and elevated temperature conditions.

Corrosion rates for chlorine dioxide were 4 to 6.5 greater than for peracetate oxidant on steel. Coupons exposed to chlorine dioxide developed a red-orange colored iron oxide coating with moderate to severe blistering and flaking. Salt water conditions did not significantly influence corrosion rate or appearance. Elevated temperature increased the peracetate oxidant corrosion rate by about 1.5 times. Chlorine dioxide corrosion decreased slightly at higher temperature, which may have been due to faster oxidant loss from outgassing or due to a heavier oxide scale formation that partially inhibited the corrosion rate.

In some embodiments, water treatment corrosion test conditions similar to those found in water treatment facilities, cooling towers and pulp & paper mills were conducted on a common pipe steel and copper to compare continuous exposure to lower concentrations of peracetate oxidant, chlorine dioxide, and chlorine bleach. Saturated oxygen from air was used as the control test for the corrosion rate of just the carrier fluid (water) in air. The peracetate oxidant was the least corrosive with rates only slightly higher than dissolved oxygen. Oxidant concentration was monitored hourly and additional oxidant was added to the carrier fluid during the test period as needed.

On steel the corrosion rate of chlorine dioxide was 1.7 to 2.1 times greater than peracetate oxidant and chlorine bleach was up to 1.5 times more corrosive than peracetate oxidant at room temperature. Increasing temperature to 140° F. increased corrosion rate of peracetate oxidant about 1.6 times while the chlorine dioxide corrosion rate doubled and the peracetic acid corrosion rate quadrupled.

On copper, chlorine dioxide was 12 times more corrosive than peracetate oxidant and bleach was 440 times more corrosive at 140° F. Corrosion of copper by peracetate oxidant was inhibited relative to oxygen in air, likely due to better passivation of the copper surface with a tighter oxide layer formed by peracetate oxidant. Bleach and chlorine dioxide tarnished the copper coupons with a green-black oxide layer while coupons in peracetate oxidant remained bright and untarnished.

In some embodiments, vapor corrosion tests reflecting vapor corrosion conditions potentially encountered in hot environments such as the vapor head space in closed tanks and pipes and in open-air paper making processes and their facilities were also conducted. Vapor corrosion is a particular problem in paper mills and cooling towers where structural steel supports and other equipment is degraded and must be replaced periodically. These tests compare continuous exposure to vapor-phase concentrations of peracetate oxidant, chlorine bleach, chlorine dioxide and peracetic acid in the head space above oxidant solutions in sealed containers. Saturated oxygen from air was used as a control test for the corrosion rate of just the carrier fluid in air. Measured corrosion rates in the vapor phase are reduced significantly using peracetate oxidant relative to bleach, chlorine dioxide and peracetic acid. The low volatility of peracetate oxidant solution (peracetate oxidant is a solid in its native form) minimizes vapor corrosion and odors from the oxidant. This behavior is in contrast to elemental chlorine, chlorine dioxide and ozone, which are gasses with very limited solubility in water at elevated temperatures, and peracetic acid, which is significantly volatile.

Vapor corrosion tests were conducted with test coupons suspended in the vapor head space in closed containers over a period of 6 hours, which was long enough to provide accurate weight loss measurements while monitoring oxidant concentration. Oxidant concentration was monitored hourly and additional oxidant was added to the carrier fluid during the test period as needed. On steel the peracetate oxidant was about 1.7 times more corrosive than air, chlorine bleach was about 8.6 times more corrosive than air, chlorine dioxide was about 11 times more corrosive than air and peracetic acid was about 5 times more corrosive than air (peracetic acid consisted of a 1:1.3 mass ratio of PAA to $H_2O_2$ in acetic acid and water).

In some embodiments, tests were conducted to evaluate the formation potential of halogenated organic oxidation byproducts with peracetate oxidant relative to other common oxidants (peracetic acid, chlorine bleach, chlorine dioxide) and a blank (no oxidant). Treatment of flowback water from a hydraulically fractured oil well and bleaching of wood pulp were conducted as test cases. Water samples were tested for total organic halide (TOX) after water treatment and bleaching processes. There was no detectable TOX formation in the treated flowback water and significantly reduced TOX formation during pulp delignification and bleaching.

In some embodiments, peracetate oxidant solution was tested for its propensity to form bromate in water containing high bromide ion concentrations that are encountered in seawater, formation water and waste water. No bromate formation was detected in the treatment of a simulated seawater composition and a production water from the oilfield under conditions that are favorable for bromate formation. In contrast, bromate formation as an oxidation byproduct is a well-known issue for oxidants such as ozone and peracetic acid.

EXAMPLES

Having now described the invention, the same will be more readily understood through reference to the following example(s), which are provided by way of illustration, and are not intended to be limiting of the present invention.

Example 1: Pond Treatment Method with Peracetate Oxidant Solution and Bleach

A 2 acre, lined evaporation pond containing about 4.1 million gallons of water (waste water from the oilfield and industrial sources) was having severe odor problems during the warm summer months due to anaerobic bacteria blooms and chemical decomposition byproduct odors. The pond was being treated with about 2100 to 4200 gallons of 12.5% chlorine bleach every three to four days to manage the odors. The water in the pond was about pH 7 and contained approximately 5% salinity, 10-14 mg/L total iron and about 400-600 mg/L suspended solids. In the summer months the water temperature ranged from about 65 to 85 degrees Fahrenheit. The pond had three modest-sized aerator fountains that were operated up to 12 hours per day.

Treatment of the pond with peracetate oxidant solution was conducted 4-5 days after a bleach treatment. The pond water appeared grey-brown with some black plumes surfacing from the bottom of the water column and odor emissions were increasing. Near the water surface the ORP was about 165 mV vs SHE, dissolved oxygen near 1 mg/L, pH 7 and temperature around 65-70° F.

Microbial content was measured using a Luminultra™ Quench Gone, Organic Modified ATP measurement method with a PhotonMaster™ luminometer and LumiCalc™ software. Before treatment the ATP concentration in the water was 6870 pg/mL at the water surface, 10,100 pg/mL in the middle of the water column and 45,700 pg/mL at the bottom of the water column. An approximate correlation between ATP concentration and bacteria cell concentration measured using standard serial dilution culture vials is provided in Table 1.

TABLE 1

| Measured ATP Concentration | Correlated Bacteria Concentration |
|---|---|
| 50 pg/mL | 1-10 cells/mL |
| 4000 pg/mL | 10,000-100,000 cells/mL |
| 10,000 pg/mL | >1 million cells/mL |
| 50,000 pg/mL | >10 million cells/mL |

A peracetate oxidant production system was configured to produce about 4.5 gallons per minute of a 4.9% peracetate oxidant solution. The output of this system was injected into the header (suction side) of the pond water circulation pumps described above. Oxidant injection was configured in this manner to greatly improve the efficiency of oxidant mixing, contact and treatment of the water. An alternate location to inject the oxidant was on the discharge side of the pumps. Approximately 75-85% of the oxidant was injected into the first pump running near 4200 gallons per minute and the second pump running near 1100 gallons per minute. The ORP and ATP concentration were monitored at various locations to monitor treatment progress.

When peracetate treatment was first started the ORP of the water at the first pump's discharge re-entering the pond (after about a 30 second residence time in the discharge pipe) was about 680 mV vs SHE. The oxidant demand was very high as indicated by a rapid consumption of oxidant in grab samples. After about 15.5 hours of treatment about 4.9 million gallons of water (120% of the pond volume) was circulated and contacted with peracetate oxidant. The first pump's discharge had a higher ORP of about 750 mV vs SHE indicating that the oxidant demand had decreased. The ORP at the far end of the pond had increased to around 600 mV and was in the 330-450 mV range over much of the rest of the pond (measurements taken around the pond's perimeter). About 20 feet downstream of the first pump's discharge the ORP was 670 mV and the ATP concentration was 2410 pg/mL. The appearance of the pond water was brown instead of grey-brown and foul odors had decreased significantly. Treatment was then turned off for the night.

The same treatment process was resumed the next morning and the first pump's discharge had an even higher ORP of about 775 mV vs SHE. The ORP of the pond was increasing slowly due to the limited injection rate of the peracetate oxidant solution. The goal was to raise the ORP of the entire pond to above 600 mV for at least 1 hour. After about 4 hours of the day's treatment the ORP readings around the pond perimeter ranged from 400 to 710 mV and the oxidant demand of the water was significantly reduced.

To accelerate reaching the 600 mV ORP goal a rapid dose of 1775 gallons of 12.5% chlorine bleach was then added near the pump intakes 6 hours into the day's peracetate oxidant treatment, which was continued. When the bleach was added the first pump's discharge water ORP increased to over 800 mV. ORP readings around the pond perimeter were in the 600-700 mV range about 1 hour after the bleach addition. The peracetate oxidant treatment and water circulation continued until 8.33 hours of total treatment time for the day had elapsed and then treatment was stopped. Water samples from the four sides of the pond were analyzed for bacteria. Measured ATP concentrations were 55, 51, 41 and 31 pg/mL, which are in the 1-10 cells/mL range for bacteria concentration. The color of the pond water was tan-brown and had relatively little odor. There was no significant grow back in the treated water samples after five months in storage at room temperature.

The two day combined water volume circulated was about 7.6 million gallons, 185% of the pond volume. Based on these results an effective treatment of a body of contaminated water is the combination of at least one pond volume, and preferably more than 1.5 pond volumes, circulated while efficiently contacting the circulated water with an oxidant added at a rate that elevates the pond's ORP to over 600 mV vs SHE for an extended period of time.

Example 2: Cooling Tower Example

An evaporative cooling tower at a municipal power plant was on a chlorine treatment program for microbiological control. The cooling tower had a water circulation rate of 60,000 gpm and a total water volume of about 906,000 gal and averaged about 3 cycles of concentration. The makeup water source was primarily river water containing some alkalinity, which resulted in a slightly alkaline pH about 7.8-8.2 in the cooling tower. The total oxidant concentration in the cooling water was maintained around 0.2 to 0.5 ppm $Cl_2$ to minimize corrosion rate and chemical costs. At this chlorine concentration and pH the ORP of the cooling water was around 500-575 mV (vs SHE), a range correlated with biostatic conditions. However, over time the microbial load in the water and on surfaces of the condenser had increased leading to lower cooling efficiency and increased microbial corrosion. Increasing exposure risk to microbes in the drift, such as *legionella*, was also a concern.

The cooling tower was shock-treated with peracetate oxidant solution for reducing the sessile microbial load at the condenser and to reduce the overall bacteria population (planktonic and sessile) in the cooling tower water circulation system and basin. Shock treatment with elevated concentrations of peracetate oxidant is enabled by its low corrosivity, high biocidal activity, elevated ORP in alkaline conditions and enhanced biocidal activity when thermally activated at the condenser (water temperature at the condenser can reach 130-160° F.). The cooling tower operating parameters and shock treatment parameters using a 5% sodium peracetate solution (designated as NaPA) are summarized in Table 2.

A two hour treatment with peracetate oxidant treatment was designed to elevate the oxidant concentration to about 20 ppm at the condenser where it is thermally activated for microbial reduction in the water and biofilm disruption, but has a corrosion rate of less than 1 mpy on copper and other sensitive metallurgy even though the ORP is elevated up to as high as 750 mV (vs SHE). The residual oxidant concentration in the water returning to the basin is approximately 10 ppm, which provides bacteria control and reduction throughout the water circulation system. Sequential dosing of additional peracetate solution on top of a 10 ppm residual in a recirculation loop also provides a synergistic antimicrobial performance improvement over just a single oxidant spike.

A 5% sodium peracetate oxidant solution is metered into the water circulation system, after the blowdown and before the heat exchanger or condenser, at a rate of 720 gallons per hour for two hours (NaPA Feed Rate in Table 2). This provides at least a two hour contact time with the oxidant for effective microbial reduction. Planktonic microbes are reduced by about 98-99.7% and heat exchange efficiency is improved. The chlorine treatment can be stopped during the shock treatment period or continued throughout without interference.

TABLE 2

| Parameter | Unit | Value |
| --- | --- | --- |
| Cooling tower volume | gal | 906,000 |
| Circulation rate | gpm | 60,000 |
| Residence time per cycle | min | 15.1 |
| Cooling tower volume | lb H2O | 7,519,800 |
| Circulation rate | lb/min | 498,000 |
| Evaporation rate | % of circ | 3.5 |
| NaPA in Evaporate | ppmw | 0.01 |
| Drift rate | % of circ | 0.1 |
| Blowdown rate | % of circ | 1.5 |
| Cycles of Conc. |  | 3.3 |
| Makeup water rate | % of circ | 5.1 |
| Makeup water rate | lb/min | 25,398 |
| Makeup water rate | gpm | 3060 |
| NaPA removal rate: drift + blowdown | lb/min | 0.080 |
| NaPA removal rate: Evaporate | lb/min | 0.00017 |
| NaPA removal rate: Consumption + Decomposition | lb/min | 4.9 |
| NaPA Total removal rate | lb/min | 5.0 |
| NaPA half life | min | 15 |
| NaPA Conc. before condenser | ppmw | 20.1 |
| NaPA conc. in cycle return | ppmw | 10.0 |
| NaPA residual in cooling tower water volume | lb | 75.2 |
| NaPA Feed Conc. | % | 5 |
| NaPA Feed Rate | gph | 719.5 |
| NaPA Treatment Time | hours | 2 |
| NaPA Total Volume Dosed | gal | 1439 |

Example 3: Paper Mill Treatment

Sodium peracetate oxidant solution is used to control microbial growth in a printing paper mill in stock preparation and white water recovery. White water entrains fiber, chemicals and microbes from the paper web. Microbes have an opportunity to propagate during extended residence time in the white water chest. Pulp sources entering the machine chest, such as boke and recovered fiber, will carry elevated microbial loads after their recovery form the paper machine process. Microbial concentrations can exceed $10^6$ to $10^7$ cells/mL, a level that reduces paper quality, accelerates biofilm growth and microbially influenced corrosion, increases paper defects and odor problems. These problems increase the frequency of down time for maintenance and increase paper reject.

Several points exist where the peracetate oxidant solution can be added to the paper mill process. Ideally the peracetate solution is added to a fluid (water and pulp) where there is a contact time of several minutes to allow for more effective microbial control in the presence of high solids and allowing for thermal activation of the peracetate in warm and hot water streams that are typical in a paper mill. The use of peracetate oxidant has virtually no impact on pH, thereby avoiding the use of a second chemical feed for pH balance as is necessary when using moderate concentrations of acidic oxidants like chlorine dioxide and peracetic acid in a closed or partially closed-loop system.

A first peracetate oxidant dose point is associated with the white water recovery. Peracetate oxidant is dosed into the inflow of the white water chest at about 20-40 ppm concentration relative to the inflow fluid volume rate. For example, a 10,000 gpm inflow rate would be injected with 8 gpm of a 5% sodium peracetate solution to provide a 40 ppm oxidant dose concentration. This amount of oxidant can provide up to about a 6 log reduction in microbial concentration depending the type and concentration of paper solids, additives, impurities and microbial species present. When the recovered white water reaches the wire pit it can potentially contain an oxidant residual when it is combined with the thick stock. If no oxidant residual is required at the wire pit due to a sensitive dye or other additive in the thick stock the amount of peracetate oxidant added to the white water can be reduced.

A second peracetate oxidant dose point is associated with the broke chest. Peracetate oxidant is dosed into the inflow of the broke tank at about 40-60 ppm concentration relative to the inflow fluid volume rate. This amount of oxidant can provide up to about a 6 log reduction in microbial concentration depending on temperature and the type and concentration of paper solids, impurities and microbial species present. When the broke reaches the blend chest it can contain an oxidant residual. If no oxidant residual is required at the blend chest the amount of peracetate oxidant added in the broke chest can be reduced.

Using the peracetate oxidant as a biocide in a paper mill process reduces the vapor corrosion rate of an oxidizing biocide to nearly the rate of air on steel around the paper machine. The loss of peracetate to evaporation is very low, which also results in greater use efficiency and reduced exposure of personnel to nuisance vapors relative to chlorine, chlorine dioxide or peracetic acid products.

Using peracetate oxidant as a biocide in producing paper grades for food packaging and totally chlorine free (TCF) paper provides unexpected advantages of imparting no odor to the paper and producing little to no halogenated byproducts.

Example 4: Disinfection of Feedstocks for Bio-Based Chemical Production

Sodium peracetate oxidant was used for microbial disinfection of polysaccharide feedstock materials used for producing succinic acid and lactic acid in a fermentation process. The peracetate is blended with the feedstock mixture in a blending tank to make an initial sodium peracetate concentration of up to about 130 ppm (by weight) and this mixture is heated to around its fermentation temperature of about 50-60° C. In this temperature range thermal activation of the peracetate oxidant occurs which increases antimicrobial activity and the rate of oxidant consumption such that the treatment is more rapidly finished and oxidant residual is eliminated before entering the fermentation stage containing the engineered microbes.

The thermally activated peracetate disinfection treatment is conducted for 30 to 90 minutes depending on the oxidant consumption rate, solids loading and particle size of the feedstock materials. The level of residual active oxidant can be monitored by ORP or by a peroxide titration method. The ORP of the active oxidant mixture can exceed 700 mV (vs SHE) during treatment while the ORP will drop significantly when the oxidant has been consumed, for example, to less than 500 mV.

After antimicrobial treatment the feedstock materials are fed to the fermenter along with other nutrients, pH buffers or additives necessary to support the fermentation process. The byproducts of the peracetate formulation, including acetate and glycerol, are readily fermented in the fermentation process and do not need to be washed or separated from the disinfected feedstock materials. After fermentation the chemical products (succinic and lactic acid) are separated from the fermentation broth, refined and purified.

Example 5: Sanitizing with Peracetate Oxidant

Example of Making a sanitizing solution: A 224.3 gal (849.5 L) volume of potable water was dispensed into a 250 gal (946 L) stainless steel day tank outfitted with a tank mixer and heater. The water was heated to 45° C. followed by rapid addition of 0.675 gal (2.55 L) of a 5% sodium peracetate solution to make 225 gal (852 L) of 150 ppm sodium peracetate sanitizing solution with an initial pH of about 8-9. The sanitizing solution was dispensed within about 5 minutes of preparation to a sprayer or clean in place system. The final pH of the spent sanitizing solution was about pH 6.5. The spent sanitizing solution was confirmed to have no residual active oxidant before discharge to the sanitary sewer.

Example of Making an Alkaline Sanitizing Solution: A 224.2 gal (848.6 L) volume of potable water was dispensed into a 250 gal (946 L) stainless steel day tank outfitted with a tank mixer and heater. The water was heated to 45° C. followed by rapid addition of 0.11 gal (0.43 L) of 20% sodium hydroxide solution and 0.675 gal (2.55 L) of a 5% sodium peracetate solution to make 225 gal (852 L) of 150 ppm sodium peracetate sanitizing solution with an initial pH of about 11.5. The sanitizing solution was dispensed within about 5 minutes of preparation to a sprayer or clean in place system. The final pH of the spent alkaline sanitizing solution was about pH 7.5-8. The spent sanitizing solution was confirmed to have no residual active oxidant before discharge to the sanitary sewer.

Example of Making an Acid Sanitizing Solution: A 224.2 gal (848.6 L) volume of potable water was dispensed into a 250 gal (946 L) stainless steel day tank outfitted with a tank mixer and heater. The water was heated to 45° C. followed by addition of 9.4 lb gal (4.3 kg) of citric acid. After the citric acid was dissolved 0.675 gal (2.55 L) of a 5% sodium peracetate solution was added to make 225 gal (852 L) of 150 ppm sodium peracetate sanitizing solution with an initial pH of about 2.8. The sanitizing solution was dispensed within about 5 minutes of preparation to a sprayer or clean in place system. The final pH of the spent alkaline sanitizing solution was about pH 3-4. The spent sanitizing solution was pH adjusted to about pH 6-7.5 with baking soda and confirmed to have no residual active oxidant before discharge to the sanitary sewer.

Example 6: Bleaching of Kraft Pulp

Side by side bleaching tests were conducted to compare the relative bleaching rate and efficiency of peracetate oxidant solution with peracetic acid and chlorine dioxide under relatively mild pulp bleaching conditions. Sodium hydroxide (ACS reagent grade), glacial acetic acid (certified ACS), 98% sulfuric acid (ACS reagent grade), 3% hydrogen peroxide (topical solution), 35% hydrogen peroxide (stabilized, Acros) ceric sulfate standard solution, 0.1 N (Fisher), sodium thiosulfate standard solution, 0.025N (HACH) and ammonium molybdate reagent (HACH) were used as received.

Sodium peracetate oxidant solution was produced by combining 7.0 mL of 3% hydrogen peroxide with 1.0 mL of distilled water, 6.5 mL of 1 molar sodium hydroxide and 0.81 mL of triacetin. The mixture was rapidly stirred and allowed to react for about 2 minutes at room temperature making a 3.7% wt/vol concentration of sodium peracetate. The sodium peracetate concentration was measured using the HACH iodometric titration method for hydrogen peroxide and adjusting for molecular weight.

A peracetic acid stock solution containing about 11-16% peracetic acid and 15-22% hydrogen peroxide was prepared by combining 20 mL of cold 35% hydrogen peroxide into 30 mL of cold glacial acetic acid. The mixture was allowed to equilibrate at room temperature in a vented container away from light for 4 days and then refrigerated for storage of up to two weeks. The actual peracetic acid and hydrogen peroxide concentrations were measured before use by the determination of hydrogen peroxide and peracetic acid in solutions method of Enviro Tech Chemical Services which incorporates titration of hydrogen peroxide with ceric sulfate and ferroin indicator followed by titration of peracetic acid with sodium thiosulfate and potassium iodide indicator.

Chlorine dioxide stock solution preparation: One AQUA-Tab 20 G chlorine dioxide tablet (Beckart Environmental, Inc.) was dissolved in 27 oz (800 mL) of distilled water in a closed polyethylene container according to the product instructions to produce up to a 0.3% solution. The yellow solution was allowed to sit for at least 1 hour before use and stored in a refrigerator. The chlorine dioxide concentration was measured prior to use by the HACH DPD method and DR900 colorimeter. Chlorine bleach (5%, Great Value brand) was measured for total chlorine concentration prior to use by the HACH DPD method and DR900 colorimeter.

Solution pH was measured using a high sodium pH electrode (Oakton) with three point calibration. ORP was measured using a platinum electrode ORP probe (Oakton) calibrated with an ORP standard (42±3 mV vs SHE, Orion 967901, Thermo Fisher). ATP (adenosine triphosphate) concentration was measured using the LuminUltra 2nd Generation metabolic ATP measurement technology with the LuminUltra™ Quench Gone-Organic Modified sampling method, a PhotonMaster Luminometer™ and LumiCalc™ software. Acid producing bacteria (ABP) and sulfate reducing bacteria (SRB) cell culture concentrations were measured with standard 1 mL serial dilutions using Intertek APB and SRB culture media, 6% salinity.

Kraft pulp was prepared from 50 lb Kraft paper (Pacon Corp.) by blending cut paper pieces in distilled water in a blender for 30-45 seconds to disperse the fibers. The pulp was drained over a screen, spread on a clean surface and air dried (ambient air less than 25% relative humidity at 20° C.) until a stable weight was obtained.

Bleaching and hand sheet casting was conducted by the following procedure. A 3.75 g portion of the dried pulp was pre-wetted in about 75 mL of distilled water. The wetted pulp was then transferred to a small blender jar and blended for 10 seconds to disperse fiber clumps and the pulp slurry was transferred to a beaker with magnetic stir bar and known volume of water. The slurry was heated in a temperature controlled water bath positioned over a magnetic stir plate. The pH of the pulp slurry was adjusted to the desired level with 4 normal sodium hydroxide or sulfuric acid solution. A volume of oxidant concentrate and additional water were added to make a 1.5% pulp consistency in a total liquid mass of 250 g. The pulp slurry was stirred throughout the bleaching time. After the bleaching process the slurry was vacuum filtered through a Buchner funnel over a medium porosity filter paper disc having a 9 cm (3.5 inch) diameter. The dewatered hand sheet was peeled off of the filter paper and air dried to a constant weight. Kappa numbers of hand sheets were measured in duplicate following the procedure described in the Mantech Inc. Kappa number determination protocol.

TABLE 3

| Entry No. | Bleach Time (min) | Oxidant | Initial Oxidant Conc. (g/L PAA equiv.) | Initial pH | Final pH | Final ORP (mV vs SHE) | Kappa No. |
|---|---|---|---|---|---|---|---|
| 1 | Unbleached | — | — | — | — | — | 30 |
| 2 | 30 | ClO$_2$ | 1.13 | 8.2 | 6.4 | 896 | 22 |
| 3 | 30 | Peracetate oxidant | 4.0 | 7.1 | 5.3 | 1025 | — |
| 4 | 30 | Peracetate oxidant | 4.0 | 8.1 | 7.1 | 768 | — |
| 5 | 30 | Peracetate oxidant | 4.0 | 8.7 | 7.3 | 690 | 24 |
| 6 | 30 | Peracetate oxidant | 4.0 | 10.0 | 8.5 | 765 | 24 |
| 7 | 30 | PAA* | 4.0 | 7.0 | 7.0 | 502 | 31 |
| 8 | 30 | PAA* | 4.0 | 8.0 | 8.0 | 406 | — |
| 9 | 30 | PAA* | 4.0 | 8.9 | 8.8 | 253 | 29 |

*PAA stock solution was measured as 11.4% PAA and 15.6% H$_2$O$_2$, pH = 1.0

Visible differences in pulp brightness were observed and Kappa number measurements were used to quantify these differences. The initial pulp (a mixture of hard and soft wood) had a Kappa number of 30. Bleaching with peracetic acid is known to be most effective near pH 7-8 with the tradeoff of promoting losses from wasteful side reactions that increase significantly above pH 7. Under the conditions of the hand sheet tests summarized in Table 1 the bleaching efficiency of peracetic acid was poor with only up to one Kappa unit reduction measured. An additional inefficiency was the need to use a large amount of amount of alkali (e.g., sodium hydroxide) to neutralize the acetic acid and peracetic acid content to raise the pH of the bleaching solution to pH 7. For example, 10.9 g/L of sodium hydroxide was needed to adjust the pH of a 4.0 g/L peracetic acid solution up to pH 7.0.

A similar issue of alkali consumption exists for chlorine dioxide, which is strongly acidic. To bleach with 1.0 g/L of chlorine dioxide at pH 8 about 1.5 g/L of sodium hydroxide was consumed, which adds a significant cost in a bleaching process. For example, bleaching with 50 lbs of ClO$_2$ per ton dry pulp would consume approximately 75 lbs of NaOH per ton dry pulp for acid neutralization.

In contrast, the natural pH of the peracetate oxidant solution when used in pulp bleaching is typically about pH 8 to 9, which falls within its optimal bleaching pH range and does not require the addition of alkali. The bleaching performance of peracetate oxidant appeared the same from pH 8 to pH 11. The bleaching rate and pulp brightness was significantly greater for peracetate oxidant at pH 8-10 over peracetic acid at pH 7-9. Only chlorine dioxide achieved a greater brightness and lower Kappa number in the same time period and pH range. However, chlorine dioxide gas was rapidly volatilized from the warm bleaching slurry while the peracetate oxidant primarily remained in solution. Peracetic acid produced a strong odor of acetic acid and peracetic acid being volatilized from the warm bleaching slurries and left a residual odor of vinegar on the pulp after air drying. There was little residual odor from the air dried pulp after bleaching with peracetate oxidant and ClO$_2$.

The increased bleaching efficiency observed for peracetate oxidant over peracetic acid is due to the efficient generation of useful reactive oxygen species in significant concentrations by the peracetate oxidant solution. It was previously demonstrated that the presence of hydrogen peroxide inhibits the bleaching activity of peracetate oxidant and peracetic acid solutions. Peracetate oxidant solution is formulated and produced in a way that makes it more active and superior as a bleaching agent over peracetic acid, particularly in pH neutral to alkaline conditions.

Raising the bleaching temperature to 90° C. and/or raising the bleaching pH to 11 had some positive effects on pulp brightness and bleaching rate. More significantly, conducting pulp bleaching with sequential doses, or charges, of peracetate oxidant at lower concentration was found to produce brighter pulp than a single charge of oxidant at a high concentration.

Example 7: TOX Formation Tests in Water

A flowback water sample was treated with peracetate oxidant solution, peracetic acid, chlorine bleach and a blank (no oxidant) at 22° C. with an excess oxidant dose concentration to provide an extended contact time between organic contaminants and elevated concentration of oxidant. The untreated water had a pH of 5.8, ORP of 135 mV vs SHE, 86 mg/L iron, turbidity of 300 FNU, an APB population of greater than 10 million cells/mL and a SRB population of greater than 10 million cells/mL. The water was a hazy tan color and had a mild hydrocarbon odor.

Four 1 L glass beakers were filled with 900 mL of flowback water and placed on a Phipps and Bird jar test apparatus. The pH of the water was adjusted slightly to pH 6.5 with 1 M NaOH and the oxidants were added to three of the jars while mixing all of them at 150 rpm for about 8 minutes. The jars were mixed at 25 rpm for another 112 minutes then mixing was stopped and the solids allowed to settle for about 60 minutes. The four water samples were decanted into amber glass bottles and preserved with sulfuric acid for total organic halide analyses, which were conducted by a third party laboratory.

TABLE 4

| Oxidant | Initial Concentration (mg/L) | TOX (mg/L) |
|---|---|---|
| Blank | 0 | BDL |
| Peracetate oxidant | 80 (as PAA) | BDL |

TABLE 4-continued

| Oxidant | Initial Concentration (mg/L) | TOX (mg/L) |
|---|---|---|
| Peracetic Acid | 80 (PAA), 112 ($H_2O_2$) | BDL |
| Chlorine Bleach | 80 | BDL |

BDL = below detection limit, less than 0.05 mg/L

Total organic halide was below detection limit in all cases indicating that TOX formation was not an issue for this flowback water sample under the treatment conditions.

Example 8: TOX Formation Tests in Pulp Bleaching

The potential of organic halide formation during pulp bleaching was compared between peracetate oxidant solution, peracetic acid and chlorine dioxide at 50° C. and 5% pulp consistency. The pulp slurries were prepared in distilled water containing 1.0% sodium chloride to simulate salt accumulation in a bleaching circuit, which can contribute to the formation of free chlorine and chlorinated byproducts in the presence of oxidizing bleaching chemicals. The pulp slurries were prepared by weighing out 45.0 g of 50 lb Kraft paper (Pacon Corp.), cutting the paper into smaller pieces (about 1 square inch), wetting the paper in 650-750 mL of distilled water containing 1.0% NaCl and pulping the mixture in a blender for about 2-3 minutes until the consistency was approximately uniform. The pulp slurry was put into a 1 L glass beaker in a heated water bath. The beakers were fitted with liquid-tight covers to minimize evaporative losses of water and oxidants. After the pulp slurry was heated the oxidant solution and additional salt water was added to make a final composition of about 855 g water, 45.0 g of air-dry pulp, 8.55 g NaCl and the oxidant. The oxidant was mixed into the pulp slurry thoroughly with a stainless steel spatula for several minutes and then mixed periodically throughout the 2 hour bleaching period. The pH of the slurry was left at the natural pH created by each oxidant in the presence of the pulp.

The amount of oxidant used in each test was enough to partially bleach the amount of lignin present so that the oxidant was the limiting reagent. When peracetate oxidant was combined with Kraft pulp the evolution of some gas was observed accompanied by rapid bleaching that was clearly visible within the first few minutes. Chlorine dioxide also bleached the pulp rapidly, but to a lesser extent because it was applied at a lower concentration due to its limited solubility and high volatility. Peracetic acid produced a large amount of gas, but was least effective at bleaching. After 2 hours at 50° C. the pulp slurries were vacuum filtered through a Buchner funnel over a medium porosity filter paper. There was no residual oxidant present in the filtrates. The four filtrate solutions recovered were put into amber glass bottles and preserved with sulfuric acid for total organic halide analyses, which were conducted by a third party laboratory.

Each of the filtrate water solutions had a different color. The filtrate from chlorine dioxide was the darkest orange, the peracetate oxidant filtrate was light yellow, the peracetic acid filtrate was pale yellow and the blank's filtrate was golden-yellow.

Peracetate oxidant formed the least amount of TOX under the bleaching conditions. Normalizing the TOX formation to the concentration of oxidant used, the peracetate oxidant formed about 2.7 times less TOX than peracetic acid and about 10.4 times less TOX than chlorine dioxide. The peracetate oxidant solution provides strong bleaching performance and greatly reduced organic halide oxidation byproduct formation potential compared to conventional bleaching agents. The peracetate oxidant can significantly reduce pollution caused by the formation of halogenated oxidation byproducts.

TABLE 5

| Oxidant | Initial Oxidant Concentration (mg/L) | TOX (mg/L) | Normalized TOX (mg/L per 1000 mg/L oxidant) |
|---|---|---|---|
| Blank | 0 | 0.68 | — |
| Peracetate oxidant | 4000 (as PAA equivalents) | 6.7 | 1.7 |
| Peracetic Acid | 4000 (PAA), 5400 ($H_2O_2$) | 17.8 | 4.5 |
| Chlorine Dioxide | 1000 | 17.7 | 17.7 |

Example 9: Analysis of Bromate Formation

Synthetic sea water was prepared by dissolving 71 grams of "Instant Ocean" in 1000 mL of distilled water according to the product directions. A produced water sample was collected from an oil well site in northeast Colorado and contained about 31 mg/L iron, 50 mg/L magnesium, 210 mg/L calcium, 89 mg/L bromide, suspended solids (appeared tan, turbid) and microbes. Water samples were treated at room temperature (18-22° C.) using a programmable Phipps and Bird jar tester equipped with flat mixing blades and 1 L beakers. The water clarification test program consisted of a 1.25 minute rapid mix at 290 rpm impeller speed, and a slow mix at 25 rpm until 60 minutes had passed. The peracetate oxidant solution was added to 800 mL of water as a slug dose of 1.6% (wt/vol) solution at the beginning of the rapid mix. For the test that included clarification the additional water clarification chemicals were added during the rapid mix period.

Each jar test water sample was analyzed for bromide and bromate using EPA method 300.1. After treatment and contact time with the oxidant water samples were put into sealed containers and refrigerated until analysis (250 mL poly bottles for bromide samples and 250 mL amber glass bottles with 2 mL of ethylenediamine preservative for bromate samples). Analyses were conducted by a third party laboratory.

Solution pH was measured using a high sodium pH electrode (Oakton) with three point calibration. ORP was measured using a platinum electrode ORP probe (Oakton) calibrated with a ORP standard (42±3 mV vs SHE, Orion 967901, Thermo Fisher). A HACH DR 900 colorimeter and corresponding procedures with the appropriate HACH reagent kits were used to measure various water parameters (iron, calcium, magnesium) after diluting samples with an appropriate amount with distilled water. Iron analysis by HACH method 10249 was modified to avoid interferences from the produced water matrix (color indicator development time was increased). The peracetate oxidant concentration was measured using the HACH iodometric titration method for hydrogen peroxide.

Table 6 shows a summary of test results for this study. Treatment tests were modeled after that used in a recent study of disinfection byproducts formed in sea water when using commercial peracetic acid products. Treatment tests were conducted by adding 25 or 100 mg/L peracetate oxidant to 800 mL water samples and monitoring the pH and ORP during the first 60 minutes of contact time with the oxidant. The pH, maximum ORP ($ORP_{max}$), bromide and bromate concentrations are reported.

For seawater samples the ORP increased to a maximum value in about 45-55 minutes and remained at an elevated level for at least 18 hours. Seawater samples were allowed to stand at room temperature for about 18 hours to provide an extended contact time with the oxidant residual before preserving for analysis. For produced water samples, the maximum ORP was reached in about 2 minutes and decreased more rapidly afterwards due to contaminants reacting with the oxidant. The produced water sample treated with 25 mg/L peracetate oxidant solution fully consumed the oxidant within an hour. The last produced water sample treated with 100 mg/L peracetate oxidant solution and clarified was treated with the additional use of a coagulant and floc aid followed by solids separation by gravity settling to produce a water-clear solution with a reduction in pH to 7.6, iron to 3.5 mg/L and calcium to 180 mg/L. Produced water samples were allowed to stand at room temperature for about 6 hours to provide an extended contact time with the oxidant residual before preserving for analysis.

No bromate formation was detected in the treatment of the simulated seawater composition and production water from the oilfield under conditions that are favorable for bromate formation. In contrast, bromate formation as an oxidation byproduct is a well-known issue for oxidants such as ozone and peracetic acid.

TABLE 6

| Water Type | Treatment | pH | $ORP_{max}$ (mV vs SHE) | Bromide (mg/L) | Bromate (mg/L) |
|---|---|---|---|---|---|
| Seawater | none | 8.1 | 412 | 116 | ND |
| Seawater | 25 mg/L peracetate oxidant | 8.1 | 903 | 136 | ND |
| Seawater | 100 mg/L peracetate oxidant | 8.2 | 930 | 119 | ND |
| Produced Water | none | 7.9 | 445 | 89.1 | ND |
| Produced Water | 25 mg/L peracetate oxidant | 8.2 | 639 | 79.0 | ND |
| Produced Water | 100 mg/L peracetate oxidant | 8.2 | 737 | 65.6 | ND |
| Produced Water | 100 mg/L peracetate oxidant with clarification | 7.5 after clarification | 769 | 77.3 | ND |

ND = non-detect

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of reducing a microbial load in contaminated cooling water in a recirculating cooling water system in which the cooling water circulates through a cooling water circulation loop including a heat exchanger where the cooling water is heated and a cooling tower where the cooling water is cooled for return circulation to the heat exchanger, and wherein the recirculating cooling water system comprises;
   a portion of the circulating cooling water being removed from the cooling water circulation loop as blowdown to remove water as it becomes more concentrated in salt, scaling minerals, microbes and other chemicals and impurities;
   a portion of the circulating cooling water being susceptible to escape from the cooling tower in drift including mist or aerosol with water and dissolved and suspended solids, chemicals and microbes; and
   makeup water being added to the circulating cooling water in the cooling water circulation loop to make up for water lost to evaporation, the drift and the blowdown, the method comprising:
   contacting in the cooling water circulation loop the contaminated cooling water containing a population of microbes with a peracetate oxidant solution; and
   mixing said contaminated water with the peracetate oxidant solution;
   and wherein:
      the peracetate oxidant solution comprising peracetate anions and a peracid, wherein the peracetate oxidant solution has a pH from about 7 to about pH 12, and wherein the peracetate oxidant solution has a molar ratio of peracetate anions to peracid ranging from about 60:1 to about 6000:1; and
      the peracetate oxidant solution has a molar of ratio of the peracetate anion to hydrogen peroxide greater than about 16:1.

2. The method of claim 1, further comprising separating the water peracetate oxidant solution mixture into at least microbes, and a water phase.

3. The method of claim 1, further comprising heating the contaminated cooling water to within a temperature range from between about 38° C. to about 95° C.

4. The method of claim 1, wherein the amount of peracetate oxidant solution used is dependent on a severity of contamination, a degree of microbial control desired and residual oxidant solution necessary for effective microbial control.

5. The method of claim 1, wherein the contacting contaminated cooling water with the peracetate oxidant solution reduces biofilms and microbial corrosion.

6. The method of claim 1, further comprising sequentially dosing the contaminated cooling water with the peracetate oxidant solution until a degree of microbial control desired is reached.

7. The method of claim 1, further comprising adding an alternative oxidant to said cooling water after said contacting with the peracetate oxidant solution.

8. The method of claim 7, wherein the alternative oxidant is selected from the group consisting of chlorine bleach, bromine, and iodine.

9. The method of claim 1, comprising introducing the peracetate oxidant solution into the cooling water circulation loop on a suction side of a water circulation pump that feeds the cooling water to the heat exchanger.

10. The method of claim 1, wherein the contacting is performed following prior treatment of the cooling water with chlorine treatment.

11. The method of claim 10, wherein the contacting comprises shock-treating the cooling tower, the shock-treating comprising introducing the peracetate solution into the cooling water in the cooling water circulation loop.

12. The method of claim 11, comprising heating the mixture of contaminated water and peracetate oxidant solution to a temperature in a range of 130° F. to 160° F.

13. The method of claim 12, wherein the pH of the peracetate oxidant solution is about pH 10 to about pH 12.

* * * * *